(12) United States Patent
Knopf et al.

(10) Patent No.: US 9,422,574 B2
(45) Date of Patent: Aug. 23, 2016

(54) MAMMALIAN EXPRESSION VECTOR

(75) Inventors: Hans-Peter Knopf, Schallstadt (DE); Burkhard Wilms, Grenzach Wyhlen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/482,117

(22) Filed: May 29, 2012

(65) Prior Publication Data
US 2012/0271040 A1   Oct. 25, 2012

Related U.S. Application Data

(63) Continuation of application No. 12/808,798, filed as application No. PCT/EP2008/067947 on Dec. 18, 2008, now abandoned.

(30) Foreign Application Priority Data

Dec. 21, 2007  (EP) .................................. 07150339

(51) Int. Cl.
*C12N 15/85* (2006.01)
(52) U.S. Cl.
CPC ..................................... *C12N 15/85* (2013.01)
(58) Field of Classification Search
CPC ............................. C12N 15/85; C12N 15/907
USPC ............................. 435/69.1, 70.1, 320.1, 358
See application file for complete search history.

(56) References Cited

U.S. PATENT DOCUMENTS

| 5,017,478 A | 5/1991 | Cashion et al. |
| 2004/0148647 A1 | 7/2004 | Enenkel et al. |
| 2006/0246540 A1 | 11/2006 | Ashkenazi |

FOREIGN PATENT DOCUMENTS

| EP | 0555203 B1 | 8/1993 |
| EP | 1293564 A1 | 3/2003 |
| WO | 01/04306 A1 | 1/2001 |
| WO | 2004/050879 A1 | 7/2004 |

OTHER PUBLICATIONS

Reff et al.; Depletion of B Cells In Vivo by a Chimeric Mouse Human Monoclonal Antibody to CD20; Blood; vol. 83, No. 2; pp. 435-445; Jan. 15, 1994.*
Lin et al: "Expression efficiency of the human thrombomodulin-encoding gene in various vector and host systems", Gene, Elsevier, 147(2):287-292 (1994).
Saulter et al: "Selection of high-producing CHO cells using NPT selection marker with reduced enzyme activity", Bioengineering, 89(5):530-538 (2005).
Reff et al: "Depletion of B cells in vivo by a chimeric mouse human monoclonal antibody to CD20", Blood; 83 (2):435-445 (1994).
Barnett et al: "Antibody production in Chinese hamster ovary cells using an impaired selectable marker", ACS Symp. Ser. 604:27-40 (1995).
Bebbington et al: "High level expression of a recombinant antibody from myeloma cells using a glutamine synthetase gene as an amplifiable selectable marker", Biotechnology, 10:169-175 (1992).
Eaton et al: "Construction and characterization of an active factor VIII variant lacking the central one-third of the molecule", Biochemistry, 25(26):8343-8347 (1986).
Grillari et al: "Analysis of alterations in gene expression after amplification of recombinant genes in CHO cells", J. Biotechnol. 87:59-65 (2001).
Hartmann et al: "Two dominant-acting selectable markers for gene transfer studies in mammalian cells", PNAS, 85:8047-8051 (1988).
Levit et al: "Definition of an efficient synthetic poly(A) site", Genes and Dev. 3(7):1019-1025 (1989).
Makrides: "Components of vectors for gene transfer and expression", Protein Expression and Purification 17:183-202 (1999).
Simonsen et al: "Isolation and expression of an altered mouse dehydrofolate reductase cDNA", PNAS, 80:2495-2499 (1983).
Neuberger: "Expression and regulation of immunoglobulin heavy chain gene transfected into lymphoid cells", EMBO J. 2(8):1373-1378 (1983).
Subramani et al: "Expression of the mouse dihydrofolate reductase complementary deoxyribonucleic acid in simian virus 40 vectors", Mol. Cell Biol. 1(9):854-864 (1981).
Trill et al: "Production of monoclonal antibodies in COS and CHO cells", Current Opinion in Biotechnology, 6:553-560 (1995).
Vieira et al: "The pUC plasmids an M13mp7-derived system for insertion mutagenesis and sequence with synthetic universal primers", Gene, 19(3):259-268 (1982).
Wurm: "Production of recombinant protein therapeutics in cultivated mammalian cells", Nature Biotechnology, 22 (11):1393-1398 (2004).
Michael Wigler et al: "Transformation of mammalian cells with genes from procaryotes and eucaryotes", Cell, vol. 16, pp. 777-785, Apr. 1979.

* cited by examiner

*Primary Examiner* — Antonio Galisteo Gonzalez
(74) *Attorney, Agent, or Firm* — James Lynch

(57) ABSTRACT

The invention provides vector nucleic acid for expressing at least one polypeptide of interest in a mammalian cell, comprising
(a) at least one expression cassette (POI) for expressing a polypeptide of interest;
(b) an expression cassette (MSM) comprising a mammalian selectable marker gene;
(c) an expression cassette (MASM) comprising a mammalian amplifiable, selectable marker gene;
wherein the expression cassette (POI) is flanked 5' by the expression cassette (MASM), the expression cassette (MSM) is located 3' from the expression cassette (POI) and wherein the expression cassettes (MASM), (POI) and (MSM) are arranged in the same 5' to 3' orientation.
Also provided are host cells, comprising said vector and methods for producing a polypeptide using respective host cells.

1 Claim, 2 Drawing Sheets

SEQUENCE LISTING

```
<160> NUMBER OF SEQ ID NOS: 16

<210> SEQ ID NO 1
<211> LENGTH: 11109
<212> TYPE: DNA
<213> ORGANISM: Artificial
<220> FEATURE:
<223> OTHER INFORMATION: Vector sequence pBW154;
<220> FEATURE:
<221> NAME/KEY: misc_feature
<222> LOCATION: (1)..(743)
<223> OTHER INFORMATION: CMV prom/enh
<220> FEATURE:
<221> NAME/KEY: misc_feature
<222> LOCATION: (825)..(1024)
<223> OTHER INFORMATION: RK-intron
<220> FEATURE:
<221> NAME/KEY: misc_feature
<222> LOCATION: (857)..(1000)
<223> OTHER INFORMATION: RK-intron region which is spliced out upon
      expression
<220> FEATURE:
<221> NAME/KEY: misc_feature
<222> LOCATION: (1054)..(1767)
<223> OTHER INFORMATION: mAB LC (originally indicated in Seq. Id. No: 1
      with symbol "v")
<220> FEATURE:
<221> NAME/KEY: misc_feature
<222> LOCATION: (1054)..(1767)
<223> OTHER INFORMATION: n is a, c, g, or t.
<220> FEATURE:
<221> NAME/KEY: misc_feature
<222> LOCATION: (1815)..(2036)
<223> OTHER INFORMATION: SV40polyA
<220> FEATURE:
<221> NAME/KEY: misc_feature
<222> LOCATION: (2367)..(3109)
<223> OTHER INFORMATION: CMV prom/enh
<220> FEATURE:
<221> NAME/KEY: misc_feature
<222> LOCATION: (3191)..(3390)
<223> OTHER INFORMATION: RK-intron
<220> FEATURE:
<221> NAME/KEY: misc_feature
<222> LOCATION: (3223)..(3366)
<223> OTHER INFORMATION: RK-intron which is spliced out upon expression
<220> FEATURE:
<221> NAME/KEY: misc_feature
<222> LOCATION: (3452)..(4864)
<223> OTHER INFORMATION: mAB HC (originally indicated in Seq. Id. No: 1
      with symbol "y")
<220> FEATURE:
<221> NAME/KEY: misc_feature
<222> LOCATION: (3452)..(4864)
<223> OTHER INFORMATION: n is a, c, g, or t.
<220> FEATURE:
<221> NAME/KEY: misc_feature
<222> LOCATION: (4931)..(5152)
<223> OTHER INFORMATION: SV40 poly A
<220> FEATURE:
<221> NAME/KEY: misc_feature
<222> LOCATION: (5247)..(5702)
<223> OTHER INFORMATION: f1 region
<220> FEATURE:
<221> NAME/KEY: misc_feature
<222> LOCATION: (5766)..(6184)
<223> OTHER INFORMATION: SV40 prom
<220> FEATURE:
```

```
<221> NAME/KEY: misc_feature
<222> LOCATION: (6229)..(7023)
<223> OTHER INFORMATION: Neomycin phosphotransferase gene
<220> FEATURE:
<221> NAME/KEY: misc_feature
<222> LOCATION: (7087)..(7135)
<223> OTHER INFORMATION: Synthetic polyA
<220> FEATURE:
<221> NAME/KEY: misc_feature
<222> LOCATION: (7546)..(8406)
<223> OTHER INFORMATION: Beta lactamase antibiotic resistance gene
<220> FEATURE:
<221> NAME/KEY: misc_feature
<222> LOCATION: (9243)..(9243)
<223> OTHER INFORMATION: Unique linearisation site
<220> FEATURE:
<221> NAME/KEY: misc_feature
<222> LOCATION: (9276)..(9623)
<223> OTHER INFORMATION: SV40prom
<220> FEATURE:
<221> NAME/KEY: misc_feature
<222> LOCATION: (9521)..(9568)
<223> OTHER INFORMATION: SV40 minimum origin of replication
<220> FEATURE:
<221> NAME/KEY: misc_feature
<222> LOCATION: (9640)..(10203)
<223> OTHER INFORMATION: DHFR gene
<220> FEATURE:
<221> NAME/KEY: misc_feature
<222> LOCATION: (9776)..(10426)
<223> OTHER INFORMATION: Intron (Donor - Acceptor)
<220> FEATURE:
<221> NAME/KEY: misc_feature
<222> LOCATION: (10910)..(11097)
<223> OTHER INFORMATION: SV40polyA

<400> SEQUENCE: 1
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca agtctccacc ccattgacgt     600
caatgggagt ttgttttggc accaaaatca acgggacttt ccaaaatgtc gtaacaactc     660
cgccccattg acgcaaatgg gcggtaggcg tgtacggtgg gaggtctata taagcagagc     720
tcgtttagtg aaccgtcaga tcgcctggag acgccatcca cgctgttttg acctccatag     780
aagacaccgg gaccgatcca gcctccgcgg ccgggaacgg tgcattggaa cgcggattcc     840
ccgtgccaag agtgacgtaa gtaccgccta tagagtctat aggcccaccc ccttggcttc     900
gttagaacgc ggctacaatt aatacataac cttatgtatc atacacatac gatttaggtg     960
acactataga ataacatcca ctttgccttt ctctccacag tgtccactc ccaggtccaa     1020 ctgcacctcg gttctatcga aaacgcgtcc accnnnnnnn nnnnnnnnnn nnnnnnnnnn     1080
nnnnnnnnnn nnnnnnnnnn nnnnnnnnnn nnnnnnnnnn nnnnnnnnnn nnnnnnnnnn     1140
nnnnnnnnnn nnnnnnnnnn nnnnnnnnnn nnnnnnnnnn nnnnnnnnnn nnnnnnnnnn     1200
nnnnnnnnnn nnnnnnnnnn nnnnnnnnnn nnnnnnnnnn nnnnnnnnnn nnnnnnnnnn     1260
```

```
nnnnnnnnnn nnnnnnnnnn nnnnnnnnnn nnnnnnnnnn nnnnnnnnnn nnnnnnnnnn      1320
nnnnnnnnnn nnnnnnnnnn nnnnnnnnnn nnnnnnnnnn nnnnnnnnnn nnnnnnnnnn      1380
nnnnnnnnnn nnnnnnnnnn nnnnnnnnnn nnnnnnnnnn nnnnnnnnnn nnnnnnnnnn      1440
nnnnnnnnnn nnnnnnnnnn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnnnn      1740
nnnnnnnnnn nnnnnnnnnn nnnnnnnngtc gacccgggcg gccgcttccc tttagtgagg      1800
gttaatgctt cgagcagaca tgataagata cattgatgag tttggacaaa ccacaactag      1860
aatgcagtga aaaaaatgct ttatttgtga aatttgtgat gctattgctt tatttgtaac      1920
cattataagc tgcaataaac aagttaacaa caacaattgc attcatttta tgtttcaggt      1980 tcaggggggag atgtgggagg ttttttaaag caagtaaaac ctctacaaat gtggtaaaat      2040
ccgataagga tcgatccggg ctggcgtaat agcgaagagg cccgcaccga tcgcccttcc      2100
caacagttgc gcagcctgaa tggcgaatgg acgcgccctg tagcggcgca ttaagcgcgg      2160
cgggtgtggt ggttacgcgc agcgtgaccg ctacacttgc cagcgcccta gcgcccgctc      2220
ctttcgcttt cttcccttcc tttctcgcca cgttcgccgg ctttccccgt caagctctaa      2280
atcgggggct ccctttaggg ttccgattta gagctttacg gcacctcgac cgcaaaaaac      2340
ttgatttggg tgatggttca cgatcttcaa tattggccat tagccatatt attcattggt      2400
tatatagcat aaatcaatat tggctattgg ccattgcata cgttgtatct atatcataat      2460
atgtacattt atattggctc atgtccaata tgaccgccat gttggcattg attattgact      2520
agttattaat agtaatcaat tacggggtca ttagttcata gcccatatat ggagttccgc      2580
gttacataac ttacggtaaa tggcccgcct ggctgaccgc ccaacgaccc ccgcccattg      2640
acgtcaataa tgacgtatgt tcccatagta acgccaatag ggactttcca ttgacgtcaa      2700
tgggtggagt atttacggta aactgcccac ttggcagtac atcaagtgta tcatatgcca      2760
agtacgcccc ctattgacgt caatgacggt aaatggcccg cctggcatta tgcccagtac      2820
atgaccttat gggactttcc tacttggcag tacatctacg tattagtcat cgctattacc      2880
atggtgatgc ggttttggca gtacatcaat gggcgtggat agcggtttga ctcacgggga      2940
tttccaagtc tccaccccat tgacgtcaat gggagtttgt tttggcacca aaatcaacgg      3000
gactttccaa aatgtcgtaa caactccgcc ccattgacgc aaatgggcgg taggcgtgta      3060
cggtgggagg tctatataag cagagctcgt ttagtgaacc gtcagatcgc ctggagacgc      3120
catccacgct gttttgacct ccatagaaga caccgggacc gatccagcct ccgcggccgg      3180
gaacggtgca ttggaacgcg gattcccgt gccaagagtg acgtaagtac cgcctataga      3240
gtctataggc ccacccccttt ggcttcgtta gaacgcggct acaattaata cataacctta      3300
tgtatcatac acatacgatt taggtgacac tatagaataa catccacttt gcctttctct      3360
ccacaggtgt ccactcccag gtccaactgc acctcggttc tatcgcgatt gaattccccg      3420
gggatcctct agggtgaccg tttgtgccac cnnnnnnnnn nnnnnnnnnn nnnnnnnnnn      3480
nnnnnnnnnn nnnnnnnnnn nnnnnnnnnn nnnnnnnnnn nnnnnnnnnn nnnnnnnnnn      3540
nnnnnnnnnn nnnnnnnnnn nnnnnnnnnn nnnnnnnnnn nnnnnnnnnn nnnnnnnnnn      3600
```

```
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnggcgcg tggtacctct agagtcgacc cgggcggccg cttcccttta gtgagggtta    4920
atgcttcgag cagacatgat aagatacatt gatgagtttg acaaaccac aactagaatg     4980 cagtgaaaaa aatgctttat ttgtgaaatt tgtgatgcta ttgctttatt tgtaaccatt    5040
ataagctgca ataaacaagt taacaacaac aattgcattc attttatgtt tcaggttcag    5100
ggggagatgt gggaggtttt ttaaagcaag taaaacctct acaaatgtgg taaaatccga    5160
taaggatcga tccgggctgg cgtaatagcg aagaggcccg caccgatcgc ccttcccaac    5220
agttgcgcag cctgaatggc gaatggacgc gccctgtagc ggcgcattaa gcgcggcggg    5280
tgtggtggtt acgcgcagcg tgaccgctac acttgccagc gccctagcgc ccgctccttt    5340
cgctttcttc ccttcctttc tcgccacgtt cgccggcttt ccccgtcaag ctctaaatcg    5400
ggggctccct ttagggttcc gatttagagc tttacggcac ctcgaccgca aaaaacttga    5460
tttgggtgat ggttcacgta gtgggccatc gccctgatag acggttttc gccctttgac     5520 gttgagtcc acgttcttta atagtggact cttgttccaa actggaacaa cactcaaccc     5580
tatctcggtc tattcttttg atttataagg gattttgccg atttcggcct attggttaaa    5640
aaatgagctg atttaacaaa tatttaacgc gaattttaac aaaatattaa cgtttacaat    5700
ttcgcctgat gcggtatttt ctccttacgc atctgtgcgg tatttcacac cgcatacgcg    5760
gatctgcgca gcaccatggc ctgaaataac ctctgaaaga ggaacttggt taggtacctt    5820
ctgaggcgga agaaccagc tgtggaatgt gtgtcagtta gggtgtggaa agtccccagg     5880
ctccccagca ggcagaagta tgcaaagcat gcatctcaat tagtcagcaa ccaggtgtgg    5940
aaagtcccca ggctccccag caggcagaag tatgcaaagc atgcatctca attagtcagc    6000
```

```
aaccatagtc ccgcccctaa ctccgcccat cccgccccta actccgccca gttccgccca   6060
ttctccgccc catggctgac taatttttt tatttatgca gaggccgagg ccgcctcggc    6120
ctctgagcta ttccagaagt agtgaggagg cttttttgga ggcctaggct tttgcaaaaa   6180
gcttgattct tctgacacaa cagtctcgaa cttaaggcta gagccaccat gattgaacaa   6240
gatggattgc acgcaggttc tccggccgct tgggtggaga ggctattcgg ctatgactgg   6300
gcacaacaga caatcggctg ctctgatgcc gccgtgttcc ggctgtcagc gcaggggcgc   6360
ccggttcttt ttgtcaagac cgacctgtcc ggtgccctga atgaactgca ggacgaggca   6420
gcgcggctat cgtggctggc cacgacgggc gttccttgcg cagctgtgct cgacgttgtc   6480
actgaagcgg gaagggactg gctgctattg ggcgaagtgc cggggcagga tcctgtcca   6540 tctcaccttg ctcctgccga aaagtatcc atcatggctg atgcaatgcg gcggctgcat   6600
acgcttgatc cggctacctg cccattcgac caccaagcga acatcgcat cgagcgagca   6660 cgtactcgga tggaagccgg tcttgtcgat caggatgatc tggacgaaga gcatcagggg   6720
ctcgcgccag ccgaactgtt cgccaggctc aaggcgcgca tgcccgacgg cgaggatctc   6780
gtcgtgaccc atggcgatgc ctgcttgccg aatatcatgg tggaaaatgg ccgcttttct   6840
ggattcatcg actgtggccg gctgggtgtg gcggaccgct atcaggacat agcgttggct   6900
acccgtgata ttgctgaaga gcttggcggc gaatgggctg accgcttcct cgtgctttac   6960
ggtatcgccg ctcccgattc gcagcgcatc gccttctatc gccttcttga cgagttcttc   7020
tgagcgggac tctggggttc gaaatgaccg accaagcgac gcccaacctg ccatcacgat   7080
ggccgcaata aaatatcttt attttcatta catctgtgtg ttggttttt gtgtgaatcg   7140 atagcgataa ggatccgcgt atggtgcact ctcagtacaa tctgctctga tgccgcatag   7200
ttaagccagc cccgacaccc gccaacaccc gctgacgcgc cctgacgggc ttgtctgctc   7260
ccggcatccg cttacagaca agctgtgacc gtctccggga gctgcatgtg tcagaggttt   7320
tcaccgtcat caccgaaacg cgcgagacga aagggcctcg tgatacgcct attttatag    7380 gttaatgtca tgataataat ggtttcttag acgtcaggtg cacttttcg gggaaatgtg   7440 cgcggaaccc ctatttgttt attttctaa atacattcaa atatgtatcc gctcatgaga   7500
caataaccct gataaatgct tcaataatat tgaaaagga agagtatgag tattcaacat   7560
ttccgtgtcg cccttattcc cttttttgcg cattttgcc ttcctgtttt tgctcaccca   7620
gaaacgctgg tgaaagtaaa agatgctgaa gatcagttgg gtgcacgagt gggttacatc   7680
gaactggatc tcaacagcgg taagatcctt gagagttttc gccccgaaga acgttttcca   7740
atgatgagca cttttaaagt tctgctatgt ggcgcggtat tatcccgtat tgacgccggg   7800
caagagcaac tcggtcgccg catacactat tctcagaatg acttggttga gtactcacca   7860
gtcacagaaa agcatcttac ggatggcatg acagtaagag aattatgcag tgctgccata   7920
accatgagtg ataacactgc ggccaactta cttctgacaa cgatcggagg accgaaggag   7980
ctaaccgctt ttttgcacaa catgggggat catgtaactc gccttgatcg ttgggaaccg   8040
gagctgaatg aagccatacc aaacgacgag cgtgacacca cgatgcctgt agcaatggca   8100
acaacgttgc gcaaactatt aactggcgaa ctacttactc tagcttcccg gcaacaatta   8160
atagactgga tggaggcgga taaagttgca ggaccacttc tgcgctcggc ccttccggct   8220
ggctggttta ttgctgataa atctggagcc ggtgagcgtg ggtctcgcgg tatcattgca   8280
gcactggggc cagatggtaa gccctcccgt atcgtagtta tctacacgac ggggagtcag   8340
```

```
gcaactatgg atgaacgaaa tagacagatc gctgagatag gtgcctcact gattaagcat   8400
tggtaactgt cagaccaagt ttactcatat atactttaga ttgatttaaa acttcatttt   8460
taatttaaaa ggatctaggt gaagatcctt tttgataatc tcatgaccaa atcccttaa    8520 cgtgagtttt cgttccactg agcgtcagac cccgtagaaa agatcaaagg atcttcttga   8580 gatcctttt ttctgcgcgt aatctgctgc ttgcaaacaa aaaaaccacc gctaccagcg    8640
gtggtttgtt tgccggatca agagctacca actcttttc cgaaggtaac tggcttcagc    8700
agagcgcaga taccaaatac tgtccttcta gtgtagccgt agttaggcca ccacttcaag   8760
aactctgtag caccgcctac atacctcgct ctgctaatcc tgttaccagt ggctgctgcc   8820
agtggcgata agtcgtgtct taccgggttg gactcaagac gatagttacc ggataaggcg   8880
cagcggtcgg gctgaacggg gggttcgtgc acacagccca gcttggagcg aacgacctac   8940
accgaactga gatacctaca gcgtgagcta tgagaaagcg ccacgcttcc cgaagggaga   9000
aaggcggaca ggtatccggt aagcggcagg gtcggaacag gagagcgcac gagggagctt   9060 ccaggggaa acgcctggta tctttatagt cctgtcgggt ttcgccacct ctgacttgag    9120
cgtcgatttt tgtgatgctc gtcaggggg cggagcctat ggaaaaacgc cagcaacgcg    9180 gccttttac ggttcctggc cttttgctgg ccttttgctc acatggctcg acagatccat    9240 ttaaatttc accgtcatca ccgaaacgcg cgaggcagct gtggaatgtg tgtcagttag    9300
ggtgtggaaa gtccccaggc tccccagcag gcagaagtat gcaaagcatg catctcaatt   9360
agtcagcaac caggtgtgga aagtccccag gctccccagc aggcagaagt atgcaaagca   9420
tgcatctcaa ttagtcagca accatagtcc cgccoctaac tccgcccatc cgcccctaa    9480 ctccgcccag ttccgcccat tctccgcccc atggctgact aattttttt atttatgcag    9540 aggccgaggc cgcctcggcc tctgagctat tccagaagta gtgaggaggc ttttttggag   9600
gcctaggctt ttgcaaaaag ctttatcccc gctgccatca tggttcgacc attgaactgc   9660
atcgtcgccg tgtcccaaga tatggggatt ggcaagaacg gagacctacc ctggcctccg   9720
ctcaggaacg agttcaagta cttccaaaga tgaccacaa cctcttcagt ggaaggtaaa    9780
cagaatctgg tgattatggg taggaaaacc tggttctcca ttcctgagaa gaatcgacct   9840
ttaaaggaca gaattaatat agttctcagt agagaactca aagaaccacc acgaggagct   9900
cattttcttg ccaaaagttt ggatgatgcc ttaagactta ttgaacaacc ggaattggca   9960
agtaaagtag acatggtttg gatagtcgga ggcagttctg tttaccagga agccatgaat  10020
caaccaggcc acctcagact cttttgtgaca aggatcatgc aggaatttga agtgacacg   10080 ttttttcccag aaattgattt ggggaaatat aaacttctcc cagaataccc aggcgtcctc  10140
tctgaggtcc aggaggaaaa aggcatcaag tataagtttg aagtctacga gaagaaagac  10200
taacaggaag atgctttcaa gttctctgct cccctcctaa agctatgcat ttttataaga  10260
ccatgggact tttgctggct ttagatcttt gtgaaggaac cttacttctg tggtgtgaca  10320
taattggaca aactacctac agagatttaa agctctaagg taaatataaa attttttaagt 10380 gtataatgtg ttaaactact gattctaatt gtttgtgtat tttagattcc aacctatgga  10440
actgatgaat gggagcagtg gtggaatgcc tttaatgagg aaaacctgtt ttgctcagaa  10500
gaaatgccat ctagtgatga tgaggctact gctgactctc aacattctac tcctccaaaa  10560
aagaagagaa aggtagaaga ccccaaggac tttccttcag aattgctaag ttttttgagt  10620
catgctgtgt ttagtaatag aactcttgct tgctttgcta tttacaccac aaaggaaaaa  10680
gctgcactgc tatacaagaa aattatggaa aaatattctg taacctttat aagtaggcat  10740
```

```
aacagttata atcataacat actgttttt cttactccac acaggcatag agtgtctgct      10800
attaataact atgctcaaaa attgtgtacc tttagctttt taatttgtaa aggggttaat      10860
aaggaatatt tgatgtatag tgccttgact agagatcata atcagccata ccacatttgt      10920
agaggtttta cttgctttaa aaacctccc acacctcccc ctgaacctga aacataaaat       10980
gaatgcaatt gttgttgtta acttgtttat tgcagcttat aatggttaca aataaagcaa      11040
tagcatcaca aatttcacaa ataaagcatt tttttcactg cattctagtt gtggtttgaa      11100
ttcggatct                                                             11109

<210> SEQ ID NO 2
<211> LENGTH: 59
<212> TYPE: DNA
<213> ORGANISM: Artificial
<220> FEATURE:
<223> OTHER INFORMATION: MCS site I; chemically synthesized

<400> SEQUENCE: 2
ctagggccca ccggtgaccg tttaaacacg tgatatccgg acaattgtcg gcgcgccgg       59

<210> SEQ ID NO 3
<211> LENGTH: 46
<212> TYPE: DNA
<213> ORGANISM: Artificial
<220> FEATURE:
<223> OTHER INFORMATION: Primer; chemically synthesized

<400> SEQUENCE: 3
gggcactacg tgccgcggat ttaaatgcgg ccgcatatgg tgcact                    46

<210> SEQ ID NO 4
<211> LENGTH: 38
<212> TYPE: DNA
<213> ORGANISM: Artificial
<220> FEATURE:
<223> OTHER INFORMATION: Primer; chemically synthesized

<400> SEQUENCE: 4
gggcacgtag tgtttattag gggagcagag aacttgaa                             38

<210> SEQ ID NO 5
<211> LENGTH: 564
<212> TYPE: DNA
<213> ORGANISM: Artificial
<220> FEATURE:
<223> OTHER INFORMATION: DHFR wildtype;

<400> SEQUENCE: 5
atggttcgac cattgaactg catcgtcgcc gtgtcccaag atatggggat tggcaagaac       60
ggagacctac cctggcctcc gctcaggaac gagttcaagt acttccaaag aatgaccaca      120
acctcttcag tggaaggtaa acagaatctg gtgattatgg gtaggaaaac ctggttctcc      180
attcctgaga agaatcgacc tttaaaggac agaattaata tagttctcag tagagaactc      240
aaagaaccac cacgaggagc tcattttctt gccaaaagtt tggatgatgc cttaagactt      300
attgaacaac cggaattggc aagtaaagta gacatggttt ggatagtcgg aggcagttct      360
gtttaccagg aagccatgaa tcaaccaggc cacctcagac tctttgtgac aaggatcatg      420
caggaatttg aaagtgacac gttttttccca gaaattgatt tggggaaata taaacttctc      480
ccagaatacc caggcgtcct ctctgaggtc caggaggaaa aaggcatcaa gtataagttt      540
```

```
gaagtctacg agaagaaaga ctaa                                      564
```

<210> SEQ ID NO 6
<211> LENGTH: 564
<212> TYPE: DNA
<213> ORGANISM: Artificial
<220> FEATURE:
<223> OTHER INFORMATION: DHFR mutant;

<400> SEQUENCE: 6

```
atggttcgac cattgaactg catcgtcgcc gtgtcccaaa atatggggat tggcaagaac    60
ggagaccgac cctggcctcc gctcaggaac gagttcaagt acttccaaag aatgaccaca   120
acctcttcag tggaaggtaa acagaatctg gtgattatgg gtaggaaaac ctggttctcc   180
attcctgaga gaatcgacc tttaaaggac agaattaata tagttctcag tagagaactc   240
aaagaaccac cacgaggagc tcattttctt gccaaaagtt tggatgatgc cttaagactt   300
attgaacaac cggaattggc aagtaaagta gacatggttt ggatagtcgg aggcagttct   360
gtttaccagg aagccatgaa tcaaccaggc cacctcagac tctttgtgac aaggatcatg   420
caggaatttg aaagtgacac gttttttccca gaattgatt tggggaaata taaacttctc   480
ccagaatacc caggcgtcct ctctgaggtc caggaggaaa aaggcatcaa gtataagttt   540
gaagtctacg agaagaaaga ctaa                                          564
```

<210> SEQ ID NO 7
<211> LENGTH: 795
<212> TYPE: DNA
<213> ORGANISM: Artificial
<220> FEATURE:
<223> OTHER INFORMATION: Neomycin resistance gene;

<400> SEQUENCE: 7

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac ccatggcgat gcctgcttgc cgaatatcat ggtgaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795
```

<210> SEQ ID NO 8
<211> LENGTH: 743
<212> TYPE: DNA
<213> ORGANISM: Artificial
<220> FEATURE:
<223> OTHER INFORMATION: CMV promoter;

<400> SEQUENCE: 8

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca tagggactt tccattgacg tcaatgggtg gagtatttac ggtaaactgc      360
ccacttggca gtacatcaag tgtatcatat gccaagtacg cccctattg acgtcaatga      420 cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca gtctccacc ccattgacgt      600 caatgggagt ttgttttggc accaaaatca acgggacttt ccaaaatgtc gtaacaactc     660
cgccccattg acgcaaatgg gcggtaggcg tgtacggtgg aggtctata taagcagagc      720 tcgtttagtg aaccgtcaga tcg                                             743

<210> SEQ ID NO 9
<211> LENGTH: 419
<212> TYPE: DNA
<213> ORGANISM: Artificial
<220> FEATURE:
<223> OTHER INFORMATION: SV40 Promoter;

<400> SEQUENCE: 9
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc cctaactccg cccagttccg cccattctc      300 cgccccatgg ctgactaatt ttttttattt atgcagaggc cgaggccgcc tcggcctctg     360
agctattcca gaagtagtga ggaggctttt ttggaggcct aggcttttgc aaaaagctt     419

<210> SEQ ID NO 10
<211> LENGTH: 222
<212> TYPE: DNA
<213> ORGANISM: Artificial
<220> FEATURE:
<223> OTHER INFORMATION: SV40 Poly A Site;

<400> SEQUENCE: 10
cagacatgat aagatacatt gatgagtttg gacaaaccac aactagaatg cagtgaaaaa      60
aatgctttat ttgtgaaatt tgtgatgcta ttgctttatt tgtaaccatt ataagctgca     120
ataaacaagt taacaacaac aattgcattc attttatgtt tcaggttcag ggggagatgt     180
gggaggtttt ttaaagcaag taaaacctct acaaatgtgg ta                        222

<210> SEQ ID NO 11
<211> LENGTH: 200
<212> TYPE: DNA
<213> ORGANISM: Artificial
<220> FEATURE:
<223> OTHER INFORMATION: RK intron;

<400> SEQUENCE: 11
```

-continued

| | |
|---|---|
| ttggaacgcg gattccccgt gccaagagtg acgtaagtac cgcctataga gtctataggc | 60 |
| ccaccccctt ggcttcgtta gaacgcggct acaattaata cataacctta tgtatcatac | 120 |
| acatacgatt taggtgacac tatagaataa catccacttt gcctttctct ccacaggtgt | 180 |
| ccactcccag gtccaactgc | 200 |

<210> SEQ ID NO 12
<211> LENGTH: 942
<212> TYPE: DNA
<213> ORGANISM: Artificial
<220> FEATURE:
<223> OTHER INFORMATION: DHFR mutant including intron;
<220> FEATURE:
<221> NAME/KEY: misc_feature
<222> LOCATION: (565)..(942)
<223> OTHER INFORMATION: intron

<400> SEQUENCE: 12

| | |
|---|---|
| atggttcgac cattgaactg catcgtcgcc gtgtcccaaa atatggggat tggcaagaac | 60 |
| ggagaccgac cctggcctcc gctcaggaac gagttcaagt acttccaaag aatgaccaca | 120 |
| acctcttcag tggaaggtaa acagaatctg gtgattatgg gtaggaaaac ctggttctcc | 180 |
| attcctgaga agaatcgacc tttaaaggac agaattaata tagttctcag tagagaactc | 240 |
| aaagaaccac cacgaggagc tcattttctt gccaaaagtt tggatgatgc cttaagactt | 300 |
| attgaacaac cggaattggc aagtaaagta gacatggttt ggatagtcgg aggcagttct | 360 |
| gtttaccagg aagccatgaa tcaaccaggc cacctcagac tctttgtgac aaggatcatg | 420 |
| caggaatttg aaagtgacac gttttttccca gaaattgatt ggggaaaata taaacttctc | 480 |
| ccagaatacc caggcgtcct ctctgaggtc caggaggaaa aaggcatcaa gtataagttt | 540 |
| gaagtctacg agaagaaaga ctaacaggaa gatgctttca gttctctgc tcccctccta | 600 |
| aagctatgca ttttttataag accatggggg atgctcgatc ccctcgcgag ttggttcagc | 660 |
| tgctgcctga ggctggacga cctcgcgag ttctaccggc agtgcaaatc cgtcggcatc | 720 |
| caggaaaacca gcagcggcta tccgcgcatc catgcccccg aactgcagga gtggggaggc | 780 |
| acgatggccg ctttggtccg gatctttgtg aaggaacctt acttctgtgg tgtgacataa | 840 |
| ttggacaaac tacctacaga gatttaaagc tctaaggtaa atataaaatt tttaagtgta | 900 |
| taatgtgtta aactactgat tctaattgtt tgtgtatttt ag | 942 |

<210> SEQ ID NO 13
<211> LENGTH: 49
<212> TYPE: DNA
<213> ORGANISM: Artificial
<220> FEATURE:
<223> OTHER INFORMATION: Synthetic poly A site; chemically synthesized

<400> SEQUENCE: 13

| | |
|---|---|
| aataaaatat ctttattttc attacatctg tgtgttggtt tttgtgtg | 49 |

<210> SEQ ID NO 14
<211> LENGTH: 861
<212> TYPE: DNA
<213> ORGANISM: Artificial
<220> FEATURE:
<223> OTHER INFORMATION: Beta lactamase antibiotic resistance gene;

<400> SEQUENCE: 14

| | |
|---|---|
| atgagtattc aacatttccg tgtcgccctt attcccttt tgcggcatt ttgccttcct | 60 |
| gtttttgctc acccagaaac gctggtgaaa gtaaaagatg ctgaagatca gttgggtgca | 120 |

-continued

```
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga ccaccacgatg   540 cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatgatgaa cgaaatagac agatcgctga gataggtgcc     840
tcactgatta agcattggta a                                              861
```

```
<210> SEQ ID NO 15
<211> LENGTH: 39
<212> TYPE: DNA
<213> ORGANISM: Artificial
<220> FEATURE:
<223> OTHER INFORMATION: MCS site II; chemically synthesized

<400> SEQUENCE: 15
ctagcctcga gaattcacgc gtggtacctc tagagtcga                            39
```

```
<210> SEQ ID NO 16
<211> LENGTH: 9210
<212> TYPE: DNA
<213> ORGANISM: Artificial
<220> FEATURE:
<223> OTHER INFORMATION: Vector sequence pBW165;
<220> FEATURE:
<221> NAME/KEY: misc_feature
<222> LOCATION: (1)..(743)
<223> OTHER INFORMATION: CMV prom/enh
<220> FEATURE:
<221> NAME/KEY: misc_feature
<222> LOCATION: (825)..(1024)
<223> OTHER INFORMATION: RK-intron
<220> FEATURE:
<221> NAME/KEY: misc_feature
<222> LOCATION: (857)..(1000)
<223> OTHER INFORMATION: RK-intron region which is spliced out upon
      expression
<220> FEATURE:
<221> NAME/KEY: variation
<222> LOCATION: (1053)..(1054)
<223> OTHER INFORMATION: insertion of mAB LC or functional fragment
      thereof
<220> FEATURE:
<221> NAME/KEY: misc_feature
<222> LOCATION: (1101)..(1322)
<223> OTHER INFORMATION: SV40polyA
<220> FEATURE:
<221> NAME/KEY: misc_feature
<222> LOCATION: (1653)..(2395)
<223> OTHER INFORMATION: CMV prom/enh
<220> FEATURE:
<221> NAME/KEY: misc_feature
<222> LOCATION: (2477)..(2676)
<223> OTHER INFORMATION: RK-intron
<220> FEATURE:
<221> NAME/KEY: misc_feature
<222> LOCATION: (2509)..(2652)
```

```
<223> OTHER INFORMATION: RK-intron region which is spliced upon
      expression
<220> FEATURE:
<221> NAME/KEY: variation
<222> LOCATION: (2750)..(2751)
<223> OTHER INFORMATION: insertion of mAB HC or functional fragment
      thereof
<220> FEATURE:
<221> NAME/KEY: misc_feature
<222> LOCATION: (2817)..(3038)
<223> OTHER INFORMATION: SV40polyA
<220> FEATURE:
<221> NAME/KEY: misc_feature
<222> LOCATION: (3133)..(3588)
<223> OTHER INFORMATION: f1 region
<220> FEATURE:
<221> NAME/KEY: misc_feature
<222> LOCATION: (3652)..(4070)
<223> OTHER INFORMATION: SV40 prom
<220> FEATURE:
<221> NAME/KEY: misc_feature
<222> LOCATION: (3968)..(4033)
<223> OTHER INFORMATION: minimum origin of replication
<220> FEATURE:
<221> NAME/KEY: misc_feature
<222> LOCATION: (4115)..(4909)
<223> OTHER INFORMATION: Neomycin phosphotransferase gene
<220> FEATURE:
<221> NAME/KEY: misc_feature
<222> LOCATION: (4973)..(5021)
<223> OTHER INFORMATION: synthetic polyA
<220> FEATURE:
<221> NAME/KEY: misc_feature
<222> LOCATION: (5432)..(6292)
<223> OTHER INFORMATION: Beta lactamase antibiotic resistance
<220> FEATURE:
<221> NAME/KEY: misc_feature
<222> LOCATION: (7170)..(7508)
<223> OTHER INFORMATION: SV40 prom
<220> FEATURE:
<221> NAME/KEY: misc_feature
<222> LOCATION: (7585)..(8148)
<223> OTHER INFORMATION: DHFR mutant
<220> FEATURE:
<221> NAME/KEY: misc_feature
<222> LOCATION: (8149)..(8526)
<223> OTHER INFORMATION: DHFR mutant intron
<220> FEATURE:
<221> NAME/KEY: misc_feature
<222> LOCATION: (9010)..(9205)
<223> OTHER INFORMATION: SV40 polyA

<400> SEQUENCE: 16
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggacttt ccattgacg tcaatgggtg gagtatttac ggtaaactgc     360
ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca agtctccacc ccattgacgt     600
caatgggagt ttgttttggc accaaaatca acgggacttt ccaaaatgtc gtaacaactc     660
cgccccattg acgcaaatgg gcggtaggcg tgtacggtgg gaggtctata taagcagagc     720
tcgtttagtg aaccgtcaga tcgcctggag acgccatcca cgctgttttg acctccatag     780
```

-continued

```
aagacaccgg gaccgatcca gcctccgcgg ccgggaacgg tgcattggaa cgcggattcc      840
ccgtgccaag agtgacgtaa gtaccgccta tagagtctat aggcccaccc ccttggcttc      900
gttagaacgc ggctacaatt aatacataac cttatgtatc atacacatac gatttaggtg      960
acactataga ataacatcca ctttgccttt ctctccacag gtgtccactc ccaggtccaa     1020
ctgcacctcg gttctatcga aaacgcgtcc accgtcgacc cgggcggccg cttcccttta     1080
gtgagggtta atgcttcgag cagacatgat aagatacatt gatgagtttg acaaaccac      1140 aactagaatg cagtgaaaaa aatgctttat ttgtgaaatt tgtgatgcta ttgctttatt     1200
tgtaaccatt ataagctgca ataaacaagt taacaacaac aattgcattc attttatgtt     1260
tcaggttcag ggggagatgt gggaggtttt ttaaagcaag taaaacctct acaaatgtgg     1320
taaaatccga taaggatcga tccgggctgg cgtaatagcg aagaggcccg caccgatcgc     1380
ccttcccaac agttgcgcag cctgaatggc gaatggacgc gccctgtagc ggcgcattaa     1440
gcgcggcggt gtggtggtt acgcgcagcg tgaccgctac acttgccagc gccctagcgc      1500
ccgctccttt cgctttcttc ccttcctttc tcgccacgtt cgccggcttt ccccgtcaag     1560
ctctaaatcg gggctccct ttaggttcc gatttagagc tttacggcac ctcgaccgca      1620
aaaaacttga tttgggtgat ggttcacgat cttcaatatt ggccattagc catattattc     1680
attggttata tagcataaat caatattggc tattggccat tgcatacgtt gtatctatat     1740
cataatatgt acatttatat tggctcatgt ccaatatgac cgccatgttg cattgatta      1800 ttgactagtt attaatagta atcaattacg gggtcattag ttcatagccc atatatggag     1860
ttccgcgtta cataacttac ggtaaatggc ccgcctggct gaccgcccaa cgacccccgc     1920
ccattgacgt caataatgac gtatgttccc atagtaacgc caatagggac tttccattga     1980
cgtcaatggg tggagtattt acggtaaact gcccacttgg cagtacatca agtgtatcat     2040
atgccaagta cgccccctat tgacgtcaat gacggtaaat ggcccgcctg gcattatgcc     2100
cagtacatga ccttatggga ctttcctact tggcagtaca tctacgtatt agtcatcgct     2160
attaccatgg tgatgcggtt ttggcagtac atcaatgggc gtggatagcg gtttgactca     2220
cggggatttc caagtctcca ccccattgac gtcaatggga gtttgttttg gcaccaaaat     2280
caacgggact ttccaaaatg tcgtaacaac tccgccccat tgacgcaaat gggcggtagg     2340
cgtgtacggt gggaggtcta tataagcaga gctcgtttag tgaaccgtca gatcgcctgg     2400
agacgccatc cacgctgttt tgacctccat agaagacacc gggaccgatc cagcctccgc     2460
ggccgggaac ggtgcattgg aacgcggatt ccccgtgcca agagtgacgt aagtaccgcc     2520
tatagagtct ataggcccac ccccttggct tcgttagaac gcggctacaa ttaatacata     2580
accttatgta tcatacacat acgatttagg tgacactata gaataacatc cactttgcct     2640
ttctctccac aggtgtccac tcccaggtcc aactgcacct cggttctatc gcgattgaat     2700
taattccccg gggatcctct agggtgaccg tttaaaacac cggtgccacc ggcgcgtggt     2760
acctctagag tcgacccggg cggccgcttc cctttagtga gggttaatgc ttcgagcaga     2820
catgataaga tacattgatg agtttggaca aaccacaact agaatgcagt gaaaaaaatg     2880
ctttatttgt gaaatttgtg atgctattgc tttatttgta accattataa gctgcaataa     2940
acaagttaac aacaacaatt gcattcattt tatgtttcag gttcaggggg agatgtggga     3000
ggttttttaa agcaagtaaa acctctacaa atgtggtaaa atcgataag gatcgatccg      3060 ggctggcgta atagcgaaga ggcccgcacc gatcgccctt cccaacagtt gcgcagcctg     3120
```

```
aatggcgaat ggacgcgccc tgtagcggcg cattaagcgc ggcgggtgtg gtggttacgc   3180
gcagcgtgac cgctacactt gccagcgccc tagcgcccgc tcctttcgct ttcttccctt   3240
cctttctcgc cacgttcgcc ggctttcccc gtcaagctct aaatcggggg ctcccttttag  3300 ggttccgatt tagagcttta cggcacctcg accgcaaaaa acttgatttg ggtgatggtt   3360
cacgtagtgg gccatcgccc tgatagacgg ttttttcgccc tttgacgttg gagtccacgt  3420
tctttaatag tggactcttg ttccaaactg gaacaacact caaccctatc tcggtctatt   3480
cttttgattt ataagggatt ttgccgattt cggcctattg gttaaaaaat gagctgattt   3540
aacaaatatt taacgcgaat tttaacaaaa tattaacgtt tacaatttcg cctgatgcgg   3600
tattttctcc ttacgcatct gtgcggtatt tcacaccgca tacgcggatc tgcgcagcac   3660
catggcctga ataacctct gaaagaggaa cttggttagg taccttctga ggcggaaaga   3720
accagctgtg gaatgtgtgt cagttagggt gtggaaagtc cccaggctcc ccagcaggca   3780
gaagtatgca aagcatgcat ctcaattagt cagcaaccag gtgtggaaag tccccaggct   3840
ccccagcagg cagaagtatg caaagcatgc atctcaatta gtcagcaacc atagtcccgc   3900
ccctaactcc gcccatcccg ccctaactc cgcccagttc cgcccattct ccgccccatg    3960
gctgactaat tttttttatt tatgcagagg ccgaggccgc ctcggcctct gagctattcc   4020
agaagtagtg aggaggcttt tttggaggcc taggcttttg caaaaagctt gattcttctg   4080
acacaacagt ctcgaactta aggctagagc caccatgatt gaacaagatg gattgcacgc   4140
aggttctccg gccgcttggg tggagaggct attcggctat gactgggcac aacagacaat   4200
cggctgctct gatgccgccg tgttccggct gtcagcgcag gggcgcccgg ttcttttttgt  4260 caagaccgac ctgtccggtg ccctgaatga actgcaggac gaggcagcgc ggctatcgtg   4320
gctggccacg acgggcgttc cttgcgcagc tgtgctcgac gttgtcactg aagcgggaag   4380
ggactggctg ctattgggcg aagtgccggg gcaggatctc ctgtcatctc accttgctcc   4440
tgccgagaaa gtatccatca tggctgatgc aatgcggcgg ctgcatacgc ttgatccggc   4500
tacctgccca ttcgaccacc aagcgaaaca tcgcatcgag cgagcacgta ctcggatgga   4560
agccggtctt gtcgatcagg atgatctgga cgaagagcat caggggctcg cgccagccga   4620
actgttcgcc aggctcaagg cgcgcatgcc cgacggcgag gatctcgtcg tgacccatgg   4680
cgatgcctgc ttgccgaata tcatggtgga aaatggccgc ttttctggat tcatcgactg   4740
tggccggctg ggtgtggcgg accgctatca ggacatagcg ttggctaccc gtgatattgc   4800
tgaagagctt ggcggcgaat gggctgaccg cttcctcgtg ctttacggta tcgccgctcc   4860
cgattcgcag cgcatcgcct tctatcgcct tcttgacgag ttcttctgag cgggactctg   4920
gggttcgaaa tgaccgacca agcgacgccc aacctgccat cacgatggcc gcaataaaat   4980
atctttattt tcattacatc tgtgtgttgg ttttttgtgt gaatcgatag cgataaggat   5040
ccgcgtatgg tgcactctca gtacaatctg ctctgatgcc gcatagttaa gccagccccg   5100
acacccgcca cacccgctg acgcgccctg acgggcttgt ctgctcccgg catccgctta   5160
cagacaagct gtgaccgtct ccgggagctg catgtgtcag aggttttcac cgtcatcacc   5220
gaaacgcgcg agacgaaagg gcctcgtgat acgcctattt ttataggtta atgtcatgat   5280
aataatggtt tcttagacgt caggtggcac ttttcgggga atgtgcgcg aacccctat    5340 ttgtttattt ttctaaatac attcaaatat gtatccgctc atgagacaat aaccctgata   5400
aatgcttcaa taatattgaa aaaggaagag tatgagtatt caacatttcc gtgtcgccct   5460
tattcccttt tttgcggcat tttgccttcc tgttttttgct cacccagaaa cgctggtgaa   5520
```

-continued

```
agtaaaagat gctgaagatc agttgggtgc acgagtgggt tacatcgaac tggatctcaa   5580
cagcggtaag atccttgaga gttttcgccc cgaagaacgt tttccaatga tgagcacttt   5640
taaagttctg ctatgtggcg cggtattatc ccgtattgac gccgggcaag agcaactcgg   5700
tcgccgcata cactattctc agaatgactt ggttgagtac tcaccagtca cagaaaagca   5760
tcttacggat ggcatgacag taagagaatt atgcagtgct gccataacca tgagtgataa   5820
cactgcggcc aacttacttc tgacaacgat cggaggaccg aaggagctaa ccgcttttt   5880 gcacaacatg gggatcatg taactcgcct tgatcgttgg gaaccggagc tgaatgaagc   5940
cataccaaac gacgagcgtg acaccacgat gcctgtagca atggcaacaa cgttgcgcaa   6000
actattaact ggcgaactac ttactctagc ttcccggcaa caattaatag actggatgga   6060
ggcggataaa gttgcaggac cacttctgcg ctcggccctt ccggctggct ggtttattgc   6120
tgataaatct ggagccggtg agcgtgggtc tcgcggtatc attgcagcac tggggccaga   6180
tggtaagccc tcccgtatcg tagttatcta cacgacgggg agtcaggcaa ctatggatga   6240
acgaaataga cagatcgctg agataggtgc ctcactgatt aagcattggt aactgtcaga   6300
ccaagtttac tcatatatac tttagattga tttaaaactt catttttaat ttaaaaggat   6360
ctaggtgaag atcctttttg ataatctcat gaccaaaatc ccttaacgtg agttttcgtt   6420
ccactgagcg tcagaccccg tagaaaagat caaaggatct tcttgagatc cttttttct   6480 gcgcgtaatc tgctgcttgc aaacaaaaaa accaccgcta ccagcggtgg tttgtttgcc   6540
ggatcaagag ctaccaactc tttttccgaa ggtaactggc ttcagcagag cgcagatacc   6600
aaatactgtc cttctagtgt agccgtagtt aggccaccac ttcaagaact ctgtagcacc   6660
gcctacatac ctcgctctgc taatcctgtt accagtggct gctgccagtg gcgataagtc   6720
gtgtcttacc gggttggact caagacgata gttaccggat aaggcgcagc ggtcgggctg   6780
aacggggggt tcgtgcacac agcccagctt ggagcgaacg acctacaccg aactgagata   6840
cctacagcgt gagctatgag aaagcgccac gcttcccgaa gggagaaagg cggacaggta   6900
tccggtaagc ggcagggtcg gaacaggaga gcgcacgagg gagcttccag ggggaaacgc   6960
ctggtatctt tatagtcctg tcgggtttcg ccacctctga cttgagcgtc gatttttgtg   7020
atgctcgtca gggggcgga gcctatggaa aaacgccagc aacgcggcct ttttacggtt   7080
cctggccttt tgctggcctt ttgctcacat ggctcgacag atccatttaa attttcaccg   7140
tcatcaccga aacgcgcgag gcagctgtgg aatgtgtgtc agttagggtg tggaaagtcc   7200
ccaggctccc cagcaggcag aagtatgcaa agcatgcatc tcaattagtc agcaaccagg   7260
tgtggaaagt ccccaggctc cccagcaggc agaagtatgc aaagcatgca tctcaattag   7320
tcagcaacca gtagtcccgcc cctaactccg cccatcccgc ccctaactcc gcccagttcc   7380
gcccattctc cgccccatgg ctgactaatt ttttttattt atgcagaggc cgaggccgcc   7440
tcggcctctg agctattcca gaagtagtga ggaggctttt ttggaggcct aggcttttgc   7500
aaaaagctaa ttcgagctcg gtaccccaa acttgacggc aatcctagcg tgaaggctgg   7560
taggatttta tccccgctgc catcatggtt cgaccattga actgcatcgt cgccgtgtcc   7620
caaaatatgg ggattggcaa gaacggagac cgaccctggc ctccgctcag gaacgagttc   7680
aagtacttcc aaagaatgac cacaacctct tcagtggaag gtaaacagaa tctggtgatt   7740
atgggtagga aaacctggtt ctccattcct gagaagaatc gacctttaaa ggacagaatt   7800
aatatagttc tcagtagaga actcaaagaa ccaccacgag gagctcattt tcttgccaaa   7860
```

-continued

```
agtttggatg atgccttaag acttattgaa caaccggaat tggcaagtaa agtagacatg   7920
gtttggatag tcggaggcag ttctgtttac caggaagcca tgaatcaacc aggccacctc   7980
agactctttg tgacaaggat catgcaggaa tttgaaagtg acacgttttt cccagaaatt   8040
gatttgggga aatataaact tctcccagaa tacccaggcg tcctctctga ggtccaggag   8100
gaaaaaggca tcaagtataa gtttgaagtc tacgagaaga aagactaaca ggaagatgct   8160
ttcaagttct ctgctcccct cctaaagcta tgcatttta taagaccatg ggggatgctc   8220
gatccctcg cgagttggtt cagctgctgc ctgaggctgg acgacctcgc ggagttctac   8280
cggcagtgca aatccgtcgg catccaggaa accagcagcg gctatccgcg catccatgcc   8340
cccgaactgc aggagtgggg aggcacgatg gccgctttgg tccggatctt tgtgaaggaa   8400
ccttacttct gtggtgtgac ataattggac aaactaccta cagagattta aagctctaag   8460
gtaaatataa aattttaag tgtataatgt gttaaactac tgattctaat tgtttgtgta    8520
ttttagattc caacctatgg aactgatgaa tgggagcagt ggtggaatgc ctttaatgag   8580
gaaaacctgt tttgctcaga agaaatgcca tctagtgatg atgaggctac tgctgactct   8640
caacattcta ctcctccaaa aagaagaga aaggtagaag accccaagga ctttccttca    8700
gaattgctaa gttttttgag tcatgctgtg tttagtaata gaactcttgc ttgctttgct   8760
atttacacca caaggaaaa agctgcactg ctatacaaga aaattatgga aaaatattct    8820
gtaacctta taagtaggca taacagttat aatcataaca tactgttttt tcttactcca    8880
cacaggcata gagtgtctgc tattaataac tatgctcaaa aattgtgtac ctttagcttt   8940
ttaatttgta aagggttaa taaggaatat ttgatgtata gtgccttgac tagagatcat    9000
aatcagccat accacatttg tagaggtttt acttgcttta aaaaacctcc cacacctccc   9060
cctgaacctg aaacataaaa tgaatgcaat tgttgttgtt aacttgttta ttgcagctta   9120
taatggttac aaataaagca atagcatcac aaatttcaca aataaagcat ttttttcact   9180
gcattctagt tgtggtttga attcggatct                                   9210
```

MAMMALIAN EXPRESSION VECTOR

This is a continuation of application Ser. No. 12/808,798 filed on Jun. 17, 2010, which is a National Stage of International Application No. PCT/EP2008/067947 filed on Dec. 18, 2008, which claims priority under 35 U.S.C. §119 to EP Application Serial No. 07150339.5 filed Dec. 21, 2007, each of which applications in its entirety is herein incorporated by reference.

The present invention pertains to a mammalian expression vector for expressing a polypeptide of interest as well as to methods for expressing a polypeptide of interest in a mammalian host cell by using a respective vector and host cells comprising said vector.

The ability to clone and express recombinant peptides and proteins in large amounts has become increasingly important in the recent years. The ability to purify high levels of proteins is important in the human pharmaceutical and biotechnological field, for example for producing protein pharmaceuticals as well as in the basic research setting, for example for crystallizing proteins to allow the determination of the three dimensional structure. Proteins that are otherwise difficult to obtain in quantity can be over-expressed in a host cell and subsequently isolated and purified.

The choice of an expression system for the production of recombinant proteins depends on many factors, including cell growth characteristics, expression levels, intracellular and extracellular expression, post-translational modifications and biological activity of the protein of interest, as well as regulatory issues and economic considerations in the production of therapeutic proteins. Key advantages of mammalian cells over other expression systems such as bacteria or yeast are the ability to carry out proper protein folding, complex N-linked glycosylation and authentic O-linked glycosylation, as well as a broad spectrum of other post-translational modifications. Due to the described advantages, mammalian cells are currently the expression system of choice for producing complex therapeutic proteins such as monoclonal antibodies. The first step in generating a recombinant cell line is the construction of an expression vector. The expression vector is the key element for driving the expression of the heterologous gene in the host cell and for providing selection markers for generating the recombinant cell line. The essential elements of mammalian expression vectors usually include a constitutive or inducible promoter capable of robust transcriptional activity; optimized mRNA processing and translational signals that usually include a Kozak sequence, a translation termination codon, mRNA cleavage and polyadenylation signals, as well as mRNA splicing signals; a transcription terminator; selection markers for the preparation of stable cell lines and for gene amplification; a prokaryotic origin of replication and selection markers for vector propagation in bacteria.

In recent years the focus of development was concentrating on the design of improved vectors for gene expression in mammalian cells. In spite of the plethora of available vectors, however, robust polypeptide/protein production in mammalian cells is still challenging. Several factors can influence recombinant expression in mammalian cells, including promoter strength, the context of the 5' untranslated and the translation initiation region, the efficiency of the 3' untranslated region, to polyadenylate and terminate transcription, the insertion site of the randomly integrated recombinant gene in the host chromosome, and the number of integrated copies of the gene that is being expressed. Increases in gene copy number are most commonly achieved by gene amplification using cells lines deficient in an enzyme such as dihydrofolate reductase (DHFR) or glutamine synthetase (GS) in conjunction with expression vectors containing genes encoding these enzymes and agents such as methotrexate (MTX), which inhibits DHFR, and methionine sulfoxamine (MSX) which inhibits GS. Using expression vectors containing the recombinant gene under control of a strong promoter and genes encoding DHFR or GS, DHFR$^+$ or GS$^+$ transfectants, respectively, are first obtained and gene amplification is then achieved by growing the transfectants in progressively increasing concentrations of MTX or MSX.

It is the object of the present invention, to provide an improved expression vector as well as an expression system for expressing a polypeptide of interest in a mammalian cell.

Accordingly, a vector nucleic acid for expressing at least one polypeptide of interest in a mammalian cell is provided, comprising (a) at least one expression cassette (POI) for expressing a polypeptide of interest;
(b) an expression cassette (MSM) comprising a mammalian selectable marker gene;
(c) an expression cassette (MASM) comprising a mammalian amplifiable, selectable marker gene;

wherein the expression cassette (POI) is flanked 5' by the expression cassette (MASM), the expression cassette (MSM) is located 3' from the expression cassette (POI) and wherein the expression cassettes (MASM), (POI) and (MSM) are arranged in the same 5' to 3' orientation.

A "vector nucleic acid" according to the present invention is a polynucleotide that carries at least one foreign nucleic acid fragment. A vector nucleic acid functions like a "molecular carrier", delivering fragments of nucleic acids respectively polynucleotides into a host cell. It comprises at least one expression cassette comprising regulatory and coding sequences. An expression cassette allows the proper expression of an incorporated polynucleotide. The expression cassettes decisive for the present invention will be subsequently described in further detail. Foreign polynucleotides e.g. encoding the polypeptide of interest may be inserted into the expression cassettes of the vector nucleic acid in order to be expressed. The vector nucleic acid according to the present invention may be present in circular or linearized form. Said site may e.g. be a multiple cloning site (MCS).

The expression cassette (POI) defines the expression cassette for expressing a polypeptide of interest. Said expression cassette (POI) either comprises the polynucleotide encoding the polypeptide of interest or comprises a site suitable for inserting a respective polynucleotide encoding the polypeptide of interest.

A "polypeptide" refers to a molecule comprising a polymer of amino acids linked together by a peptide bond(s). Polypeptides include polypeptides of any length, including proteins (for example, having more than 50 amino acids) and peptides (for example, having 2-49 amino acids). Polypeptides include proteins and/or peptides of any activity or bioactivity. Suitable examples are outlined below.

The expression cassette (MSM) defines the expression cassette comprising a mammalian selectable marker gene. Mammalian selectable marker genes allow the selection of mammalian host cells comprising said genes and thus of mammalian host cells comprising the vector. Suitable examples are described in detail below.

The expression cassette (MASM) defines the expression cassette comprising a mammalian amplifiable, selectable marker gene. Mammalian, amplifiable, selectable marker genes allow selection of vector-containing mammalian host cells as well as gene amplification. Suitable examples are described in detail below.

The terms "5'" and "3'" is a convention used to describe features of a nucleic acid sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, DNA sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left hand side, and 3' (downstream) indicates genetic elements positioned towards the right hand side, when following this convention.

The arrangement and orientation of the expression cassettes present in the vector of the invention is important. According to the teachings of the present invention, the expression cassette (POI) is flanked 5' by the expression cassette (MASM). Accordingly, the expression cassette (MASM) is located 5' adjacent to the expression cassette (POI) and in close proximity thereto. Of course, vector backbone sequences may separate the expression cassettes (MASM) and (POI). However, preferably, no other expression cassette is located between the expression cassette (MASM) and the expression cassette (POI). The expression cassette (MSM) is located 3' from the expression cassette (POI). Further expression cassettes may be inserted between the expression cassettes (POI) and (MSM), such as e.g. an additional expression cassette (POI') for expressing an additional polypeptide of interest (described in further detail below). The expression cassettes (MASM), (POI) and (MSM) are all arranged in the same 5' to 3' orientation. The inventors found, that this particular vector nucleic acid configuration allows the fast generation of high yielding cell lines.

According to one alternative, the expression cassette (POI) does not comprise the polynucleotide encoding the polypeptide of interest. Thus, an expression vector with an "empty" expression cassette (POI) is provided. However, said polynucleotide encoding the polypeptide of interest can be incorporated into the expression cassette (POI) by using appropriate cloning methods, for example by using restriction enzymes in order to insert the polynucleotide encoding the polypeptide of interest into the expression cassette (POI). For this purpose the expression cassette (POI) may comprise e.g. a multiple cloning site (MCS) which can e.g. be used in all reading frames. Suitable MCS sites are described in detail below. A respective "empty" vector nucleic acid can e.g. be provided to customers, which then insert their specific polynucleotide of interest to be expressed into the expression cassette (POI). The expression cassette (POI) may also comprise a replacement polynucleotide or a stuffer nucleic acid sequence, which can be excised and replaced by the polynucleotide encoding the polypeptide of interest. The present invention also provides a vector nucleic acid as described above, comprising an expression cassette (POI) comprising the polynucleotide encoding the polypeptide of interest. This embodiment pertains basically to the final expression vector nucleic acid that is transfected for expression into the host cell.

A polynucleotide is a polymer of nucleotides which are usually linked from one deoxyribose or ribose to another. The term "polynucleotide" does not comprise any size restrictions and also encompasses polynucleotides comprising modifications, in particular modified nucleotides.

According to one embodiment, the vector nucleic acid is circular and the expression cassette (MSM) is arranged 3' of the expression cassette (POI) and the expression cassette (MASM) is arranged 3' of the expression cassette (MSM). As an alternative description of a circular vector according to the teachings of the present invention is a circular vector nucleic acid for expressing at least one polypeptide of interest in a mammalian cell, comprising (a) at least one expression cassette (POI) for expressing a polypeptide of interest;
(b) an expression cassette (MSM) comprising a mammalian selectable marker gene;
(c) an expression cassette (MASM) comprising a mammalian amplifiable, selectable marker gene;

wherein the expression cassette (MSM) is arranged 3' of the expression cassette (POI) and the expression cassette (MASM) is arranged 3' of the expression cassette (MSM) and wherein the expression cassettes (MASM), (POI) and (MSM) are arranged in the same 5' to 3' orientation.

The vector nucleic acid can be transfected into the host cell in its circular form. Supercoiled vector molecules usually will be converted into linear molecules within the nucleus due to the activity of endo- and exonucleases. However, linearization of the vector nucleic acid before transfection often improves the efficiency of a stable transfection. This also as the point of linearization may be controlled if the vector is linearized prior to transfection.

Hence, according to one embodiment of the present invention the expression vector comprises a predefined restriction site, which can be used for linearization of the vector nucleic acid prior to transfection. Intelligent placement of said linearization restriction site is important, because said restriction site determines where the vector nucleic acid is opened/linearized and thus determines the order/arrangement of the expression cassettes when the construct is integrated into the genome of the mammalian cell.

Accordingly, the vector nucleic acid may comprise a linearization restriction site for linearizing the vector, wherein said linearization restriction site is located between the expression cassettes (MSM) and (MASM). Preferably, said linearization restriction site is unique and is only once present in the expression vector nucleic acid. E.g. a linearization restriction site can be used that is recognized by a restriction enzyme having a low cutting frequency in order to patronize that the vector is only cleaved at the linearization restriction site but not (or only rarely) e.g. within the expression cassette(s) or the vector backbone. This can e.g. be encouraged by providing a restriction site for a restriction enzyme having a recognition sequence of more than six base pairs or which recognizes sequences that are under-represented in chromosomal DNA. A suitable example is the SwaI enzyme and the vector may therefore incorporate a SwaI recognition site as unique linearization restriction site. In case said linearization restriction site is present more than once in the vector nucleic acid sequence (including the polynucleotides encoding the polypeptide of interest), or in case a restriction enzyme is used which cuts several times in the vector nucleic acid sequence, it is also within the scope of the present invention to e.g. alter/mutate the restriction sites besides the linearization restriction site which is located between the expression cassettes (MSM) and (MASM), in order to eliminate those additional restriction sites and to obtain a unique or at least rare linearization restriction site.

In case the vector is used as a standard expression vector intended e.g. as a tool for the expression of several different polypeptides, it is advantageous to provide a linearization restriction site comprising multiple recognition sites for enzymes having a low cutting frequency. The restriction enzymes chosen for linearization should preferably not cut within the expression cassettes for the selectable markers or other vector backbone sequences in order to ensure that the enzyme cuts only once for proper linearization of the vector. By providing a linearization restriction site comprising multiple recognition sites for restriction enzymes having a low cutting frequency, the user may chose a suitable restriction enzyme for linearization from the provided options in order to securely avoid restriction within the polynucleotide encoding the polypeptide of interest. However, as is outlined above, additional restriction sites may be mutated or a partial restriction digest could be performed.

Placing the linearization restriction site between the expression cassette (MSM) and the expression cassette (MASM) has the effect that the expression cassette (POI) (and further expression cassettes for expressing the polypeptides of interest—if present) is flanked 5' by the expression cassette (MASM). The expression cassette (MSM) is located 3' of the expression cassette (POI) upon linearization. Thereby, the expression cassettes (MSM) and (MASM) are separated upon linearization of the circular vector nucleic acid. If an expression cassette (PSM) for a bacterial selection marker is present (see below), the linearization restriction site is preferably placed between the expression cassettes (PSM) and (MASM). This has the effect that the bacterial selection marker gene is 3' and thus "outside" of the "mammalian" parts of the linearized vector nucleic acid. This arrangement is favorable since bacterial genes are presumably not advantageous for mammalian expression as bacterial sequences may lead to increased methylation or other silencing effects in the mammalian cells.

Non-limiting examples for mammalian selectable marker genes that can be comprised in the expression cassette (MSM) include antibiotic resistance genes e.g. conferring resistance to G418; hygromycin (hyg or hph, commercially available from Life Technologies, Inc. Gaithesboro, Md.); neomycin (neo, commercially available from Life Technologies, Inc. Gaithesboro, Md.); zeocin (Sh Ble, commercially available from Pharmingen, San Diego Calif.); puromycin (pac, puromycin-N-acetyl-transferase, available from Clontech, Palo Alto Calif.), ouabain (oua, available from Pharmingen) and blasticidin (available from Invitrogen). Respective mammalian selectable marker genes are well known and allow the selection of mammalian host cells comprising said genes and thus of host cells comprising the vector. The term "gene" as used herein also refers to a natural or synthetic polynucleotide encoding a functional variant of the selectable marker providing the intended resistance. Hence, also truncated or mutated versions of a wild type gene or synthetic polynucleotides are encompassed as long as they provide the intended resistance. According to a preferred embodiment, said expression cassette (MSM) comprises a gene encoding an enzymatically functional neomycin phosphotransferase (I or II). This embodiment works well in combination with the use of a gene encoding an enzymatically functional DHFR as an amplifiable selectable marker gene.

Amplifiable, selectable mammalian marker genes allow selection of vector-containing mammalian host cells as well as gene amplification. A non-limiting example for an amplifiable, selectable mammalian marker gene is the dihydrofolate reductase (DHFR) gene. Other systems currently in use are among others the glutamine synthetase (gs) system (Bebbington et al., 1992) and the histidinol driven selection system (Hartmann and Mulligan, 1988). These amplifiable markers are also selectable markers and can thus be used to select those cells that obtained the vector. DHFR and glutamine synthetase provide good results. In both cases selection usually occurs in the absence of the appropriate metabolite (hypoxanthine and thymidine in case of DHFR, glutamine in the case of GS), preventing growth of non-transformed cells. With amplifiable systems such as the DHFR system, expression of a recombinant protein can be increased by exposing the cells to certain agents promoting gene amplification such as antifolates (e.g. methotrexate (MTX)) in case of the DHFR system. A suitable inhibitor for GS promoting gene amplification is methionine sulphoximine (MSX). Exposure to MSX also results in gene amplification. According to one embodiment, said expression cassette (MASM) comprises a gene encoding an enzymatically functional glutamine synthetase (GS) or a dihydrofolate reductase (DHFR).

According to one embodiment, said expression cassette (MSM) comprises a gene encoding an enzymatically functional neomycin phosphotransferase and said expression cassette (MASM) comprises a gene encoding an enzymatically functional dihydrofolate reductase (DHFR).

The vector may comprise at least one additional expression cassette (POI') for expressing an additional polypeptide of interest. Said additional expression cassette (POI') is located between the expression cassette (POI) and the expression cassette (MSM). Said expression cassette (POI') is arranged in the same 5' to 3' orientation as the expression cassettes (POI) and (MSM). According to one embodiment, it comprises the polynucleotide encoding the additional polypeptide of interest.

Accordingly, the vector nucleic acid according to the present invention can comprise more than one expression cassette for expressing polypeptides of interest. Therefore, it is also possible that several expression cassettes ((POI), (POI'), (POI") etc.) for expressing different polypeptides of interest are arranged in the expression vector nucleic acid according to the present invention. These expression cassettes are flanked 5' by the expression cassette (MASM) and 3' by the expression cassette (MSM). Hence, the present invention also provides a vector nucleic acid comprising more than one expression cassette encoding e.g. subunits of dimeric or higher order multimeric proteins. Expression cassettes encoding different subunits of a multimeric protein, each incorporated in a different expression cassette can be placed adjacent to each other. For multimeric proteins encoded by at least two distinct genes (for instance, immunoglobulin light and heavy chains or functional fragments thereof such as at least the variable regions of the immunoglobulin light and heavy chains), the polynucleotides encoding the desired subunits of the polypeptide of interest are inserted in the expression cassettes (POI) and (POI'). A respective embodiment using at least two expression cassettes (POI) and (POI') for expressing polypeptides of interest is particularly advantageous for expressing immunoglobulin molecules such as antibodies or functional fragments thereof. Accordingly, a vector nucleic acid is provided for expressing an immunoglobulin molecule comprising in each expression cassette (POI) and (POI') a polynucleotide encoding either a light or a heavy chain of an immunoglobulin molecule or fragments thereof, wherein each expression cassette (POI) and (POI') comprises one of said polynucleotides. Accordingly, the expression cassette (POI) can either comprise the polynucleotide for expressing the light chain, or the polynucleotide for expressing the heavy chain of the immunoglobulin molecule.

According to one preferred embodiment, the expression cassette (POI) comprises the polynucleotide encoding at least part of the light chain of said immunoglobulin molecule or a functional fragment thereof and the expression cassette (POI') comprises a polynucleotide encoding at least part of the heavy chain of said immunoglobulin molecule or a functional fragment thereof. To arrange the expression cassette for the light chain 5' to the expression cassette of the heavy chain proved to be beneficial regarding the expression rate of the immunoglobulin molecules. According to one embodiment, the expression vector nucleic acid is designed such, that the expression cassette(s) already comprises a polynucleotide encoding at least part of the constant regions of an immunoglobulin molecule. The polynucleotide fragments encoding the variable parts of the immunoglobulin molecules can then be inserted by the user/customer into the expression cassettes by using appropriate cloning strategies in order to obtain the final expression vector.

The expression cassettes present in the expression vector according to the present invention are designed such that they allow the expression of the incorporated polynucleotides/genes in mammalian cells. For this purpose the expression cassettes usually comprise the necessary regulatory sequences, such as a promoter and/or a transcription termination sequence such as a poly A site.

Vectors used for expressing polypeptides of interest usually contain transcriptional control elements suitable to drive transcription such as e.g. promoters, enhancers, polyadenylation signals, transcription pausing or termination signals as elements of an expression cassette. For proper expression of the polypeptides, suitable translational control elements are preferably included in the vector, such as e.g. 5' untranslated regions leading to 5' cap structures suitable for recruiting ribosomes and stop codons to terminate the translation process. In particular, the polynucleotide serving as the selectable marker genes as well as the polynucleotide encoding the polypeptide of interest can be transcribed under the control of transcription elements present in appropriate promoters. The resultant transcripts of the selectable marker genes and that of the polypeptide of interest harbour functional translation elements that facilitate substantial levels of protein expression (i.e. translation) and proper translation termination. A functional expression unit, capable of properly driving the expression of an incorporated polynucleotide is also referred to as an "expression cassette" herein. Preferably, it comprises a 3' UTR region.

Accordingly, vector nucleic acids are provided wherein the expression cassettes comprise at least one promoter and/or promoter/enhancer element. Although the physical boundaries between these two control elements are not always clear, the term "promoter" usually refers to a site on the nucleic acid molecule to which an RNA polymerase and/or any associated factors binds and at which transcription is initiated. Enhancers potentiate promoter activity, temporarily as well as spatially. Many promoters are transcriptionally active in a wide range of cell types. Promoters can be divided in two classes, those that function constitutively and those that are regulated by induction or derepression. Promoters used for high-level production of proteins in mammalian cells should be strong and preferably active in a wide range of cell types to permit a qualitative and quantitative evaluation of the recombinant polypeptide. The promoter can be selected from the group consisting of an SV40 promoter, a CMV promoter, an EF1alpha promoter, a RSV promoter, a BROAD3 promoter, a murine rosa 26 promoter, a pCEFL promoter and a β-actin promoter. Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter and EF1a. Good results are achieved with the expression vector of the present invention when the promoter and/or enhancer is either obtained from CMV and/or SV40.

According to one embodiment, the expression cassette(s) for expressing the polypeptide(s) of interest comprise(s) a stronger promoter and/or enhancer than the expression cassettes for expressing the selectable markers. This arrangement has the effect that more transcript for the polypeptide of interest is generated than for the selection markers. It is advantageous that the production of the polypeptide of interest which is secreted is dominant over the production of the selection markers, since the individual cell capacity for producing heterologous proteins is not unlimited and should thus be focused to the polypeptide of interest.

According to one embodiment, the expression cassettes (POI) and (POI') (if present) which is/are used for expressing the polypeptide of interest comprise a CMV promoter/enhancer. Specific examples are described in detail below. The expression cassettes (MSM) and (MASM), which preferably express the DHFR and the neomycin marker genes, comprise a SV40 promoter or a SV40 promoter/enhancer. The CMV promoter is known to be one of the strongest promoters available for mammalian expression and leads to a very good expression rate. It is considered to give significantly more transcript than the SV40 promoter.

Furthermore, the expression cassettes may comprise an appropriate transcription termination site. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

Most eukaryotic nascent mRNAs possess a poly A tail at their 3' end which is added during a complex process that involves cleavage of the primary transcript and a coupled polyadenylation reaction. The polyA tail is advantageous for mRNA stability and transferability. Hence, the expression cassettes of the vector according to the present invention usually comprise a polyadenylation site. There are several efficient polyA signals that can be used in mammalian expression vectors, including those derived from bovine growth hormone (bgh), mouse beta-globin, the SV40 early transcription unit and the Herpes simplex virus thymidine kinase gene. However, also synthetic polyadenylation sites are known (see e.g. the pCl-neo expression vector of Promega which is based on Levitt el al, 1989, Genes Dev. 3, (7): 1019-1025). The polyadenylation site can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCl-neo expression vector of Promega which is based on Levitt el al, 1989, Genes Dev. 3, (7): 1019-1025) and a bgh polyA site (bovine growth hormone).

The expression cassettes may comprise an enhancer (see above) and/or an intron. According to one embodiment, the expression cassette(s) for expressing the polypeptide of interest comprise an intron. Most genes from higher eukaryotes contain introns which are removed during RNA processing. It is found, that genomic constructs are expressed more efficiently in transgenic systems than identical constructs lacking introns. Usually, introns are placed at the 5' end of the open reading frame. Accordingly, an intron may be comprised in the expression cassette(s) for expressing the polypeptide(s) of interest in order to increase the expression rate. Said intron may be located between the promoter and or promoter/enhancer element(s) and the 5' end of the open reading frame of the polypeptide to be expressed. Hence, a vector nucleic acid is provided, wherein at least the expression cassette (POI) comprises an intron which is arranged between the promoter and the start codon of the polynucleotide for expressing the polypeptide of interest. Several suitable introns are known in the state of the art that can be used in conjunction with the present invention.

According to one embodiment, the intron used in the expression cassettes for expressing the polypeptides of interest, is a synthetic intron such as the SIS or the RK intron. The RK intron is a strong synthetic intron which is preferably placed before the ATG startcodon of the gene of interest. The RK intron consists of the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen)).

Furthermore, it is surprisingly found that the placement of an intron at the 3' end of the open reading frame of the DHFR gene has advantageous effects on the expression/amplification rate of the construct. The intron used in the DHFR expression cassette is leading to a smaller, non functional variant of the DHFR gene (Grillari et al., 2001, J. Biotechnol. 87, 59-65). Thereby the expression level of the DHFR gene is lowered. This leads to increased sensitivity for MTX and more stringent selection conditions. Accordingly, a vector nucleic acid is provided, wherein the expression cassette (MASM) comprises an intron which is located 3' of the amplifiable selectable marker gene. A suitable intron may be obtained from the pSV2-DHFR vector (see e.g. above).

Said vector may comprise at least one additional expression cassette (PSM) comprising a prokaryotic selectable marker gene. Said expression cassette (PSM) is located between the expression cassettes (MSM) and (MASM). Said selectable marker may provide a resistance to antibiotics such as e.g. ampicillin, kanamycin, tetracycline and/or chloramphenicol. Said expression cassette (PSM) is preferably arranged in the same 5' to 3' orientation as the other expression cassettes (POI), (MSM) and (MASM).

The DHFR gene works as a marker and a gene amplification gene. Selection may occur by culturing the cells in the absence of the appropriate metabolites (hypoxanthine and thymidine) thereby preventing growth of non-transformed cells. With the DHFR system, expression of the polypeptides of interest can be increased by exposing the cells to antifolates such as for example methotrexate (MTX), a drug that blocks the activity of DHFR. After a certain time of exposure to MTX the majority of cells die, but a small number of cells usually survive that overproduce DHFR. Upon MTX treatment, ramped upwards in concentration, the surviving cells may frequently contain up to several hundred to a few thousand copies of the integrated vector embedded in chromosomes that are frequently elongated. Most respectively amplified cells produce more recombinant protein than the unamplified cells.

Several suitable DHFR enzymes and accordingly genes are known in the prior art that can be used in conjunction with the present invention. The DHFR may be a wildtype DHFR or a functional variant or derivative thereof. The term a "variant" or "derivative" include DHFR enzymes having one or more amino acid sequence exchanges (e.g. deletions, substitutions or additions) with respect to the amino acid sequence of the respective DHFR enzyme, fusion proteins comprising a DHFR enzyme or functional fragment thereof and DHFR enzymes which have been modified to provide an additional structure and/or function, as well as functional fragments of the foregoing, which still have at least one function of a DHFR enzyme. The DHFR gene is preferably selected from the group consisting of wildtype DHFR, a DHFR variant having a reduced MTX sensitivity compared to wildtype DHFR and a DHFR variant having an enhanced MTX sensitivity compared to wildtype DHFR. According to one embodiment, the DHFR gene is the wild type DHFR gene. According to a different embodiment, the DHFR gene encodes a less functional variant of DHFR. This leads to an increased sensitivity for MTX and more stringent selection conditions. This can be achieved e.g. by placing an intron at the 3' end of the DHFR gene (see above). A different alternative could rely on the use of a DHFR mutant/variant having a higher sensitivity towards MTX than the wildtype DHFR. These embodiments are particularly beneficial in case the vector is used in host cells which are DHFR.

In case one desires to use the DHFR system in host cells incorporating a copy of the DHFR gene in their own genome (e.g. CHO DHFR$^+$), it is preferred that a mutant/variant of the DHFR gene is used, which is less sensitive towards antifolates such as MTX than the wildtype DHFR and is thus to a certain extent antifolate respectively MTX-resistant. E.g. due to mutations in the gene the sensitivity of the DHFR gene towards MTX can be significantly reduced so that said variant can be used at higher antifolate (MTX) concentrations. Said less antifolate and in particular MTX sensitive DHFR variant can e.g. possess a reduced antifolate/MTX binding affinity. Respective DHFR variants can be used to "overtitrate" endogenous DHFR expression in wild type cell lines. Respective "resistant" or less sensitive DHFR variants are well known in the prior art.

The expression vector can be selected from the group consisting of
(a) a circular or linear vector nucleic acid comprising the following genetic elements in the indicated arrangement, wherein the 5' to 3' direction is indicated by the →:
  I. Promoter of the (MASM) expression cassette (→)
  II. Gene encoding the mammalian amplifiable selectable marker of the (MASM) expression cassette (→)
  III. Optionally an intron of the (MASM) expression cassette (→)
  IV. PolyA site of the (MASM) expression cassette (→)
  V. Promoter of the (POI) expression cassette (→)
  VI. Intron of the (POI) expression cassette (→)
  VII. Polynucleotide encoding a polypeptide of interest, which is inserted in the (POI) expression cassette (→)
  VIII. PolyA site of the (POI) expression cassette (→)
  IX. Promoter of the (POI') expression cassette (→)
  X. Intron of the (POI') expression cassette (→)

XI. Polynucleotide encoding an additional polypeptide of interest, which is inserted in the (POI') expression cassette (→)
XII. PolyA site of the (POI') expression cassette (→)
XIII. Promoter of the (MSM) expression cassette (→)
XIV. Gene encoding the mammalian selectable marker of the (MSM) expression cassette (→)
XV. PolyA site of the (MSM) expression cassette (→)
XVI. PSM expression cassette (→) or (←)
XVII. Linearization restriction site if the vector nucleic acid is circular;
(b) a vector nucleic acid as shown as Seq. ID No. 1 or Seq. ID No. 16 or a derivative thereof, comprising the same configuration respectively arrangement of genetic elements.

A preferred embodiment of variant (a) in its circular form is shown in FIG. 1 and corresponding Table. 1.

The vector according to the present invention can be obtained by arranging the expression cassettes in the proper order and orientation as is described in detail above. Arrangement of the expression cassettes/genetic elements can be done by using suitable restriction enzymes and cloning strategies in order to assemble the expression vector. Accordingly, also a method for producing a vector nucleic acid as described above is provided, wherein said method comprises arranging at least the following genetic elements
(a) at least one expression cassette (POI) for expressing a polypeptide of interest;
(b) an expression cassette (MSM) comprising a mammalian selectable marker gene;
(c) an expression cassette (MASM) comprising a mammalian amplifiable, selectable marker gene;
such that the expression cassette (POI) is flanked 5' by the expression cassette (MASM), the expression cassette (MSM) is located 3' from the expression cassette (POI) and wherein the expression cassettes (MASM), (POI) and (MSM) are arranged in the same 5' to 3' orientation.

In case a circular vector nucleic acid is produced, the genetic elements are assembled such that the expression cassette (MSM) is accordingly located 3' of the expression cassette (POI) and the expression cassette (MASM) is located 3' of the expression cassette (MSM).

The vector according to the present invention can be used for expressing the polypeptide of interest in many different mammalian host cells. The expression vector of the present invention is usually integrated into and maintained in the genome. There are two main formats of host cells, cultures of adherent cells and suspension cultures. Suspension cultures are preferred. Most established cell lines maintain their anchorage-dependent character unless special efforts are undertaken to adapt them to the suspension growth. Commercially available media formulations facilitate the transition. Basically any mammalian host cells can be used in conjunction with the present invention as long as they allow the expression of a polypeptide. Suitable mammalian host cells for the purposes of the present invention include but are not limited to cells derived from mice (e.g. COP, L, C127, Sp2/0, NS-0, NS-1, At20 or NIH3T3), rats (PC12, PC12h, GH3, MtT), hamsters (e.g. BHK, CHO and DHFR gene defective CHO), monkeys (e.g. COS1, COS3, COS7, CV1 and Vero) and humans (e.g. Hela, HEK-293, retina-derived PER-C6, cells derived from diploid fibroblasts, myeloma cells and HepG2). Preferably, the host cell is a CHO cell. The vector construction according to the present invention is particularly suitable for producing polypeptides in rodent cells such as CHO and DHFR gene defective CHO cells.

Also provided are mammalian host cells, comprising the expression vector according to the present invention. Also provided is a stable cell line, comprising an expression vector according to the present invention or a segment thereof in the genome. The segment shall comprise at least the expression cassettes decisive for the present invention. As the vector and its characteristics as well as suitable host cells are described in detail above, we refer to the above disclosure. Accordingly, also a method for producing a host cell as described above is provided, wherein the host cell is transfected with the vector nucleic acid according to at least one of the claims 1 to 16.

There are several appropriate methods known in the prior art for introducing an expression vector into a mammalian host cell. Respective methods include but are not limited to calcium phosphate transfection, electroporation, lipofection, biolistic- and polymer-mediated genes transfer. Suitable host cells are described above.

After introduction of the expression vector nucleic acid into the host cell(s), the obtained transformants are cultured under selective conditions suitable for assaying the expression of the mammalian selectable marker gene enclosed in the expression cassette (MSM). This means, that for example when the mammalian selectable marker gene is an antibiotic resistance gene, transformants are cultured in a medium containing the corresponding antibiotic active in mammalian cells and the transformants which are viable under such conditions are selected, thus enabling the obtainment of transformants which express the marker gene and thus incorporated the vector. Additionally, a second selection step may be performed by culturing the transformants in a selection medium adapted for selecting the amplifiable, selectable marker gene comprised in the expression cassette (MASM). E.g. in case DHFR is used as an amplifiable, selectable marker gene, the transformants can be cultured in a nucleotide or purine-free medium in the presence of a DHFR inhibitor.

In case an inducible promoter is used in at least one expression cassette, a corresponding induction signal should be provided in order to commence expression of the polypeptide.

In order to make use of the DHFR selection/amplification system, said host cells may be cultured in the presence of a DHFR inhibitor. Suitable DHFR inhibitors are antifolates such as e.g. MTX. The concentration of antifolate/MTX used depends on the host cell and the DHFR variant incorporated in the vector. The concentration range can be chosen for multistep amplification procedures in DHFR⁻ host cells for example at values around 5 nM-20 nM ranging to values of 500 nM to 1000 nM or even higher for secondary or further amplification steps. For DHFR⁺ cells starting concentrations are usually higher in the range of 100 nM to 750 nM, preferably 500 nM in the first steps and 500 nM to 1000 nM and above for further amplification steps. Suitable DHFR variants are described above.

In order to make use of the GS selection/amplification system said host cells may be cultured in the presence of e.g. MSX. The concentration of MSX used depends on the host cell. The concentration range can be chosen between from about 15 to 150 μM, 20 to 100 μM and 25 to 50 μM. These ranges are particularly suitable for NSO and CHO cells.

With the expression vector according to the present invention, several different polypeptides of interest may be expressed/produced. The term polypeptide refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity or bioactivity, including e.g. bioactive polypeptides such as enzymatic proteins or peptides (e.g. proteases, kinases, phosphatases), receptor proteins or peptides, transporter proteins or peptides, bactericidal and/or endotoxin-binding proteins, structural proteins or peptides, immune polypeptides, toxins, antibiotics, hormones, growth factors, vaccines or the like. Said polypeptide may be selected from the group consisting of peptide hormones, interleukins, tissue plasminogen activators, cytokines, immunoglobulins, in particular antibodies or antibody fragments or variants thereof. Said immunoglobulin can be of any isotype. Very often IgG (e.g. IgG1) molecules are produced/needed as therapeutic proteins. An antibody fragment is any fragment of an antibody comprising at least 20 amino acids from said whole antibody, preferably at least 100 amino acids, which at least still has an antigen binding capacity. The antibody fragment may comprise the binding region of the antibody such as a Fab fragment, a F(ab)2 fragment, multibodies comprising multiple binding domains such as diabodies, triabodies or tetrabodies, single domain antibodies or affibodies. An antibody variant is a derivative of an antibody or antibody fragment having the same binding function but e.g. an altered amino acid sequence. Said antibody and/or antibody fragment may comprise a murine light chain, human light chain, humanized light chain, human heavy chain and/or murine heavy chain as well as active fragments or derivatives thereof. Hence, it can be e.g. murine, humane, chimeric or humanized.

The present invention also provides methods of producing a polypeptide of interest, said method comprising culturing at least one host cell comprising a vector nucleic acid according to the present invention in a cell culture medium under conditions allowing the expression of said polypeptide of interest.

In a next step, said polypeptide can be isolated/harvested from the cell culture. The expressed polypeptide of interest may be obtained by disrupting the host cells. The polypeptides may also be expressed, e.g. secreted into the culture medium and can be obtained therefrom. Also combinations of the respective methods are possible. Thereby, products, in particular polypeptides can be produced and obtained/isolated efficiently with high yield. The obtained polypeptide may also be subject to further processing steps such as e.g. purification and/or modification steps in order to produce the product of interest in the desired quality.

According to one alternative, said polypeptide of interest is secreted into the cell culture medium and subsequently isolated from the cell culture medium. The polypeptide is preferably an immunoglobulin molecule such as an antibody or a functional fragment thereof. In order to promote secretion of the polypeptide of interest a leader sequence can be used. Preferably, the leader sequence of an immunoglobulin molecule is used.

The expression vector according to the present invention as well as suitable host cells and polypeptides of interest are described in detail above; we refer to the above disclosure.

The method for producing the polypeptide of interest may comprise at least one of the following steps:
  isolating the polypeptide of interest from said cell culture medium and/or from said host cell; and/or
  processing the isolated polypeptide of interest.

The polypeptide of interest produced in accordance with the invention may be recovered, further purified, isolated and/or modified by methods known in the art. For example, the product may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

According to one embodiment which is in particular advantageous for the production of pharmaceutical proteins/peptides, the host cell is cultured in suspension under serum-free conditions. The obtained polypeptide can afterwards be purified, e.g. by purifying the polypeptide present in the cell culture supernatant by using chromatographic methods (e.g. affinity purification).

Polypeptides produced according to the method of the present invention depict good stability properties. The results also show that the polypeptides are expressed in a functional form and hence in the right conformation. Accordingly, the invention also provides polypeptides obtained by the production method according to the present invention using the expression vector described in detail above. As is outlined above, polypeptides are obtained with a good yield. The polypeptide is preferably an immunoglobulin molecule such as an antibody or a functional fragment thereof.

Figure 1:
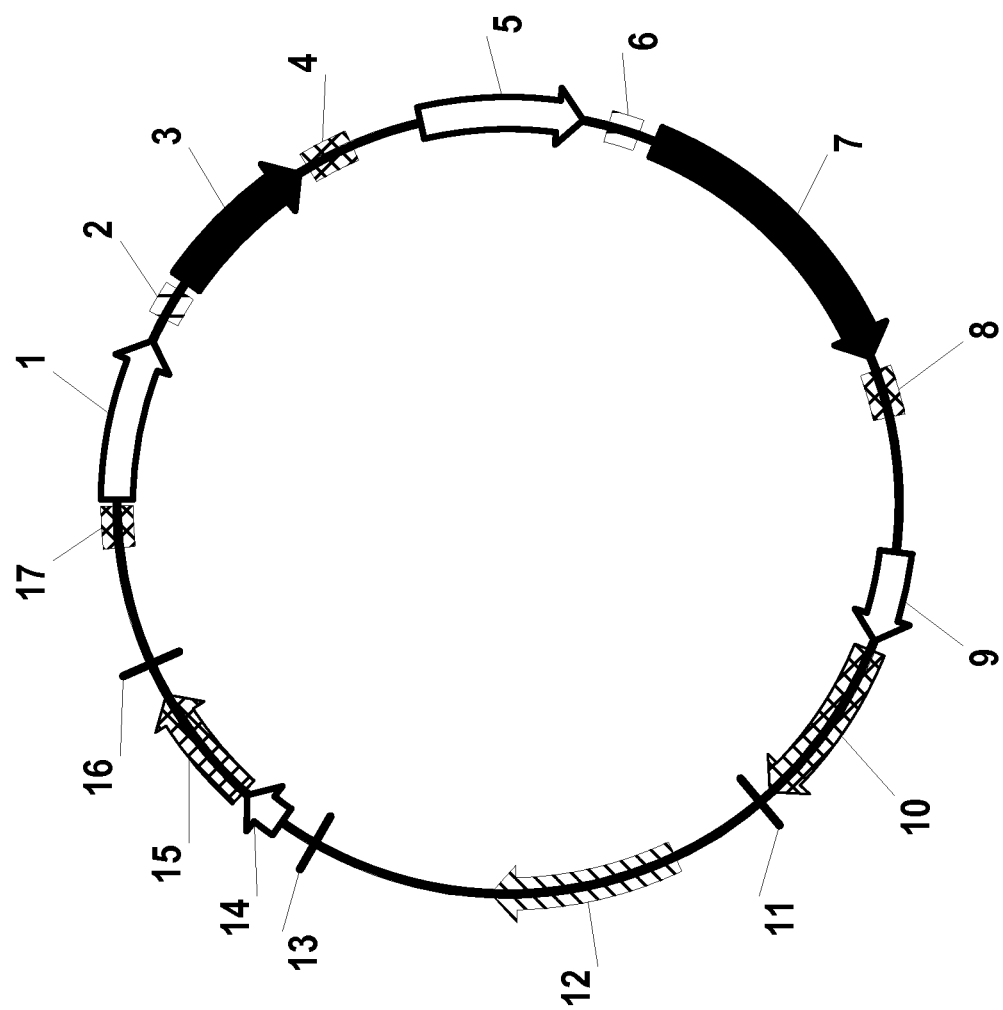
FIG. 1 shows a circular vector nucleic acid according to a preferred embodiment of the present invention.
Figure 2:
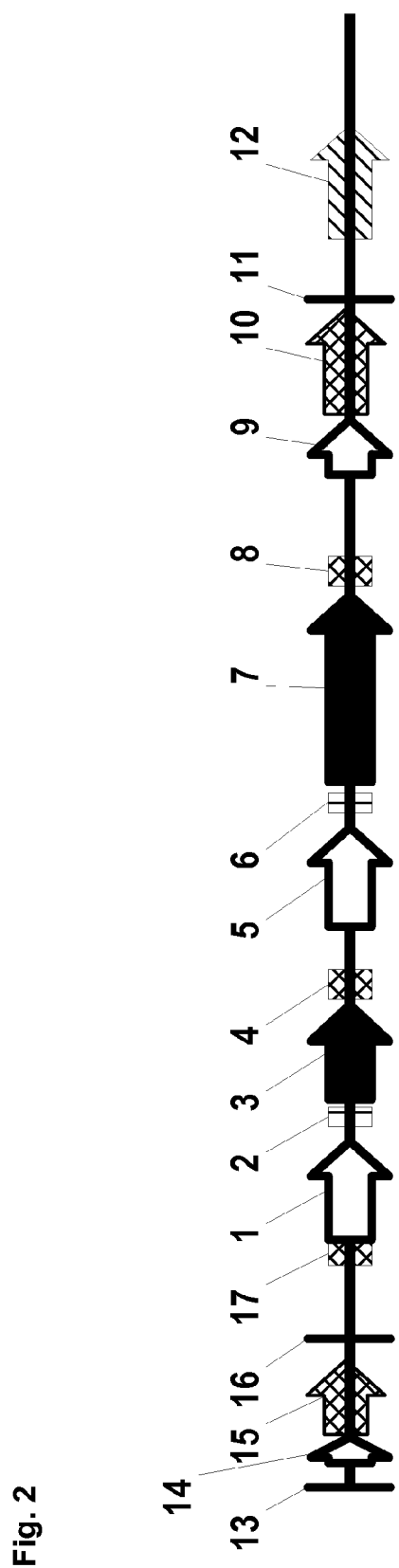
FIG. 2 shows the linearized version of the vector nucleic acid according to FIG. 1 in order to demonstrate the influence of the position of the linearization restriction site.

The numbers 1 to 17 shown in FIGS. 1 and 2 indicate the genetic elements/characteristics of the vector nucleic acid and are described in detail in the subsequent table 1. If not otherwise defined, the white arrows characterize promoters or promoter/enhancer elements; the stripped boxes characterize intron elements, the black arrows symbolize the polynucleotides for expressing the polypeptide of interest; the checkered boxes characterize the polyA site; the checkered arrows the mammalian marker genes of the expression cassette (MSM) and (MASM); the striped arrow the prokaryotic selectable marker gene. As can be seen, all genetic elements are arranged in the same 5' to 3' orientation (indicated by the direction of the arrow). The vector nucleic acids pBW147, pBW154 and pBW160, which are described in further detail below, are respectively constructed.

TABLE 1 orientation and arrangement of the genetic elements according to a vector nucleic acid as shown in FIG. 1 and 2

| Numbering in FIG. 1 and 2 | Genetic element |
|---|---|
| 1 | Promoter of the (POI) expression cassette (diagrammed by the white arrow). It is e.g. a CMV promoter/enhancer. |
| 2 | Intron of the (POI) expression cassette (diagrammed by the striped box). It is e.g. a RK-intron, as described above. |
| 3 | Polynucleotide encoding a polypeptide of interest, which is inserted in the (POI) expression cassette (diagrammed by the black arrow). According to the shown embodiment, it is the light chain of a monoclonal antibody (mAB-LC). |

TABLE 1-continued orientation and arrangement of the genetic elements according to a vector nucleic acid as shown in FIG. 1 and 2

| Numbering in FIG. 1 and 2 | Genetic element |
|---|---|
| 4 | PolyA site of the (POI) expression cassette (diagrammed by the checkered box). It is e.g. a SV40 PolyA site. |
| 5 | Promoter of the (POI') expression cassette (diagrammed by the white arrow). It is e.g. a CMV promoter/enhancer. |
| 6 | Intron of the (POI') expression cassette (diagrammed by the striped box). It is e.g. a RK-intron, as described above. |
| 7 | Polynucleotide encoding an additional polypeptide of interest, which is inserted in the (POI') expression cassette (diagrammed by the black arrow). According to the shown embodiment, it is the heavy chain of a monoclonal antibody (mAB-HC). |
| 8 | PolyA site of the (POI') expression cassette (diagrammed by the checkered box). It is e.g. a SV40 PolyA site. |
| 9 | Promoter of the (MSM) expression cassette (diagrammed by the white arrow). It is e.g. a SV40 promoter/enhancer. |
| 10 | Gene encoding the mammalian selectable marker of the (MSM) expression cassette (diagrammed by the checkered arrow). It is e.g. the neo gene. |
| 11 | PolyA site of the (MSM) expression cassette (diagrammed by the bar). It is e.g. a synthetic PolyA site as described above. |
| 12 | PSM expression cassette (diagrammed by the striped arrow). It can e.g. comprise a prokaryotic selectable marker gene providing a resistance against ampicillin. |
| 13 | Linearization restriction site (diagrammed by the bar). Said site is preferably a unique restriction site. |
| 14 | Promoter of the (MASM) expression cassette (diagrammed by the white arrow). It is e.g. a SV40 promoter. |
| 15 | Gene encoding the mammalian amplifiable selectable marker of the (MASM) expression cassette (diagrammed by the checkered arrow). It is e.g. the DHFR gene. |
| 16 | Intron in the (MASM) expression cassette (diagrammed by the bar). This intron is optionally present. |
| 17 | PolyA site of the (MASM) expression cassette (diagrammed by the checkered box). It is e.g. a SV40 PolyA site. |

Subsequently, suitable examples for the described vector elements are given, which are, however, non-limiting.

As mammalian amplifiable selectable marker the use of DHFR is preferred. A suitable example of a wildtype mouse DHFR polynucleotide is provided with Seq. ID No. 5 which is preferably used in conjunction with the DHFR⁻ host cells. A suitable mutant form of DHFR is provided with Seq. ID No. 6. A respective mutant form is preferably used together with the DHFR+ cells. Seq. ID No. 12 shows a mutant DHFR including an intron suitable for further increasing the selection pressure (see above). Also functional variants or fragments of the foregoing can be used.

As mammalian selectable marker gene the use of neo is preferred. A suitable sequence is provided with Seq. ID No. 7. Also functional variants or fragments thereof can be used.

As a promoter sequence for driving the expression of the polypeptide of interest the use of a CMV promoter is preferred. A suitable sequence is provided with Seq. ID No. 8. Also functional variants or fragments thereof can be used.

As a promoter sequence for driving the expression of the selectable marker genes MSM and MASM the use of SV40 promoter is preferred. A suitable sequence is provided with Seq. ID No. 9. Also functional variants or fragments thereof can be used.

As a polyadenylation sequence for the polypeptides of interest and/or the MASM a SV40 poly A site can be used. A suitable sequence is shown as Seq. ID No. 10. Also functional variants or fragments thereof or a reversed orientation (late or early SV40 poly A site) can be used.

As intron sequence for the expression cassette (POI) encoding the polypeptide of interest an Rk intron may be used. A suitable sequence is provided with Seq. ID No. 11. Also functional variants or fragments thereof can be used.

As synthetic polyadenylation site which can be used e.g. in conjunction with the mammalian selectable marker (MSM) is shown as Seq. ID No. 13. Also functional variants or fragments thereof can be used.

A suitable bacterial selectable marker (PSM) is e.g. the beta-lactamase gene which provides ampicillin resistance. A suitable sequence is provided with Seq. ID No. 14. Also functional variants or fragments thereof can be used.

Furthermore, the vector nucleic acid may comprise at least one multiple cloning site (MCS) for inserting e.g. a polynucleotide encoding a polypeptide of interest. MCS can be provided 3' and 5' of the polynucleotide encoding the polypeptide of interest. Suitable MCS sites are provided as Seq. ID No. 4 (preferably located at the 5' site/region) and Seq. ID No. 15 (preferably located at the 3' site/region). These MCS sites can be used e.g. in order to introduce the polynucleotide encoding the polypeptide of interest.

Particularly preferred vector nucleic acids are shown as Seq. ID No. 1 (comprising the wildtype DHFR gene, said vector is particularly useful for the DHFR− system) and Seq. ID No. 16 (comprising a mutated DHFR gene, said vector is particularly useful for the DHFR+ system).

All references cited herein are incorporated by reference and thus form part of the present disclosure.

EXAMPLES

The present invention is now described by means of non-limiting examples, which however, constitute preferred embodiments of the present invention.

I. Cell Culture Methods and Transfection

Subsequently, appropriate methods for transfecting and culturing the host cells according to the present invention for expressing a polypeptide of interest are described by means of examples.

Example 1

Cell Culturing

CHO cells are cultivated in a suitable CHO medium such as e.g. ExCell81134 (obtained from SAFC Biosciences). Cells are passaged 2-3 times per week into fresh media and are maintained in logarithmic growth phase throughout the study.

Example 2

Transfection Strategy

For transfection, parental CHO cells in exponential growth phase with a viability over 90% are used. Transfections by lipofection are done using the DMRIE-C reactant according to the instructions of the manufacturer (Invitrogen). The cell amount is adjusted to $1 \times 10^6$ cells in OptiMEM I medium (Invitrogen). For lipofection, 2 µg or 4 µg of the expression vector and 4 µl of the DMRIE-C reagent are mixed together for 28 min at room temperature and added to the cells for 4 h at 37° C. Cells are then diluted to $2 \times 10^5$ cells/ml culture medium and incubated for 2 days at 37° C. and 5% CO2.

Example 3

Neomycin Selection and Gene Amplification

The neomycin selection marker located on the expression vector nucleic acid allows selection for G418 resistance. For selection of transfectants, cells are cultivated in the presence of 0.8 mg/ml G418 (Invitrogen) for approximately two weeks. Two weeks after transfection and G418 selection, pool populations consisting predominantly of G418 resistant cells emerge. Cells are then cultivated in the absence of nucleotides for about two weeks. Gene amplification is then initiated by the addition of 20 nM MTX to the culture medium. After three weeks of cultivation, an amplified heterogeneous cell pool is generated. The DHFR (dihydrofolate reductase) selection/amplification marker allows amplification of the DHFR gene as well as of the transgene by adding the folic acid analogue methotrexate (MTX) to the culture media, resulting in increased titers for transfection pools. After crisis recovery, pools then undergo a second and a third amplification step using higher MTX concentration each for approximately two weeks (100 nM and 500 nM MTX). At each step cells are frozen after pool recovery.

Example 4

Establishment of Clonal Cell Lines

To obtain a clonal cell line (i.e., a cell line derived from a single cell), the pool of stably transfected cells can be diluted and seeded out in 96 well plates with a cell density of 0.3-0.5 cells per well (limited dilution). Cells forming a distinct colony are scaled up using standard procedures. Eventually, individual clones are evaluated for recombinant polypeptide expression, with the highest producers being retained after cultivation and analysis. From these candidates, the cell line with appropriate growth and productivity characteristics is chosen for production of the recombinant protein. The productivity can usually be further improved by establishing/adapting the culturing conditions i.e. by adding additives such as peptones.

II. Vector Constructions

Several vector assemblies according to the teachings of the present invention are feasible. As the individual elements of the vector are known in the prior art, suitable vectors can be assembled e.g. by sequencing or amplification and appropriate cloning of the basic genetic elements and expression cassettes in the desired orientation. Respective cloning methods are state of the art and also the sequence of the genetic elements described above are described in the prior art. Subsequently, the generation of several vector constructs are described by way of example. However, it is understood by those of skill in the art that several other embodiments and ways to obtain respective vectors are suitable and readily available.

In order to facilitate understanding of the arrangement of the vector constructs described herein by way of example and their precursor vectors, tables 1 and 2 provide an overview over the main genetic elements comprised in these vectors, their order and orientation. Of course, only the main elements are shown, the vectors may, however, comprise additional genetic elements or backbone sequences. Each column in the table represents one vector construct. From the top row to the bottom row the genetic elements of the expression cassettes are listed in the order of their arrangement and their orientation on the vector. As the described vectors are circular, the element shown in the last row of each column is in fact adjacent to the genetic element shown in the first row (of course, backbone sequences may be present). The orientation of each genetic element is indicated by the arrows. The arrowhead points to the 3' direction of the respective genetic element.

TABLE 2

| order of the genetic elements in the precursor vectors | | | |
|---|---|---|---|
| pBW133 10416 bp | pBW139 9213 bp | pBW146 9247 bp | pBW159 11122 bp |
| CMVprom/enh → | CMVprom/enh → | CMVprom/enh, comprising a SpeI (153) restriction site → | CMVprom/enh → |
| RK-intron → | RK-intron → | RK-intron → | RK-intron → |
| mAB-LC → | mAB-LC → | mAB-LC → | mAB-LC → |
| MCS I | MCS | MCS | MCS |

TABLE 2-continued order of the genetic elements in the precursor vectors

| pBW133 10416 bp | pBW139 9213 bp | pBW146 9247 bp | pBW159 11122 bp |
|---|---|---|---|
| SV40polyA → | SV40polyA → | SV40polyA → | SV40polyA → |
| DraIII restriction site (2365) | CMV prom/enhan → | CMV prom/enhan comprising a SpeI restriction site (2519) → | CMV prom/enhan → |
| DHFR* carrying a ScaI restriction site (2870); reverse orientation ← | RK-intron → | RK-intron → | RK-intron → |
| SV40prom/enhan; reverse orientation ← | MCS | MCS2 | mAB-HC → |
| DraIII restriction site (3651) | mAB-HC → | mAB-HC → | MCS |
| SV40prom/enhan → | MCS | MCS | T3 promoter |
| Neo → | SV40polyA → | T3 promoter | SV40polyA → |
| CMV prom/enhan → | Phage f1 region comprising a DraIII restriction site (5456) → | SV40polyA → | Phage f1 region → |
| RK-intron → | SV40prom/enhan → | Phage f1 region → | SV40prom/enhan → |
| MCS2 | Neo → | SV40prom/enhan comprising a SV40 minimum origin of replication → | Neo → |
| mAB-HC → | SV40polyA → | Neo → | Synth Poly A |
| SV40polyA → | Amp comprising a ScaI restriction site (7828) → | Synth polyA | Amp → |
| Amp carrying ScaI (9031) → | BglII restriction site (9209), 5' to the CMV prom/enh | Amp → | 3 pA sites |
|  |  | BglII restriction site (9243), 5' adjacent of the CMVprom/enh | intron |
|  |  |  | DHFR; reverse orientation ← SV40prom; reverse orientation ← SwaI restriction site (11113) |

TABLE 3 order of the genetic elements in the expression vectors

| pBW147 11053 bp | pBW154 11109 bp | pBW160 11122 bp |
|---|---|---|
| CMVprom/enh, comprising a SpeI restriction site (153) → | CMVprom/enh → | CMVprom/enh → |
| RK-intron → | RK-intron → | RK-intron → |
| mAB-LC → | mAB-LC → | mAB-LC → |
| SV40polyA → | SV40polyA → | SV40polyA → |
| CMV prom/enhan comprising a SpeI restriction site (2519) → | CMV prom/enhan → | CMV prom/enhan → |
| RK-intron → | RK-intron → | RK-intron → |
| mAB-HC → | mAB-HC → | mAB-HC → |
| SV40polyA → | SV40polyA → | SV40polyA → |
| SV40prom/enhan → | SV40prom/enhan → | SV40prom/enhan → |
| Neo → | Neo → | Neo → |
| Synth polyA | Synth polyA | Synth polyA |
| Amp → | Amp → | Amp → |
| Swa I restriction site (9288) | SwaI restriction site (9243) | SwaI restriction site (9256) |
| SV40prom/enhan → | SV40 prom → | SV40 prom → |
| DHFR* → | DHFR → | DHFR → |
| Bgh pA site → | Intron | Intron |
|  | SV40polyA | SV40polyA |

The abbreviations in the above tables 1 to 3 and in FIGS. 1 and 2 have the regular meanings as apparent for the person of skill in the art and as described above, and have in particular the following meanings:

MCS=multiple cloning site mAB-HC=monoclonal antibody heavy chain mAB-LC=monoclonal antibody light chain intron=see Grillari et al, 2001, 3. Biotechnol. 87, 59-65 prom/enh=promoter/enhancer

Example 5

Construction of Expression Vector pBW147

In this setup the tandem configuration of mAB genes and the DHFR* (mutant variant having a lower sensitivity to MTX than the wild type DHFR) combined with the bgh pA-site, is tested. The DHFR* cassette is placed 5' before the expression cassette (POI), comprising the mAB-LC, so that all open reading frames are placed in one reading direction. The assembly of pBW147 is shown in table 3.

pBW147 can be constructed from pBW133 (please also refer to table 2). The construction of pBW147 is described herein.

Construction of pBW133

The vector constructions described below are based on the commercially available pCl-neo expression vector (Promega Cooperation, USA). The complete DNA sequence is publicly available (GenBank/EMBL Accession number: U47120). A new multiple cloning site is introduced in pClneo.

The two strands of the multiple cloning site are synthesized de novo. pClneo is cut with NheI and XmaI. The old MCS is removed by gel electrophoresis. The new multiple cloning site is synthesized in the way that the terminal 4 nucleotides of the 5' end of the antisense strand and the 3' terminal end of upper DNA strand are not synthesized. After annealing of both strands compatible ends for NheI and XmaI are created.

The sequence of the new multiple cloning site is as follows (see Seq. ID No. 2):

| ApaISgrAI | | | | |
|---|---|---|---|---|
| AgeI | PmeI | EcoRV | PshAI | |
| EcoO109I | BstEII | PmlI | BspEI | AscI |

The resulting plasmid of the ligation of pClneo with the new MCS is deemed pCl-neo-2 for description purposes. pCl-neo-2 is further modified by introducing the pRK intron from pRK5 (BD PharMingen). Therefore, pCl-neo-2 is digested with ApaI. Blunt ends are created by T4 polymerase treatment. Then the plasmid is digested with NdeI. pRK5 is digested with NdeI and NruI (blunt end cutter). The RK intron containing fragment is isolated and ligated with the pClneo2 backbone. The resulting plasmid is pClneo2RK.

To bring both expression cassettes on one vector, the vector pClneoDHFR*-RK can be obtained. pClneoDHFR*-RK is obtained as follows:

The DHFR* expression cassette is amplified by PCR from vector pCHI-LC (Simulect SP2/0 light chain expression vector). The primers are BB35 (GGGCACTACGTGC-CGCGGATTTAAATGCGGCCGCATATGGTGCACT—Seq. ID No. 3) and BB36 (GGGCACGTAGTGTTTATT-AGGGGAGCAGAGAACTTGAA—Seq. ID No. 4).

The PCR fragment is cloned into pClneoRK via DraIII restriction digestion giving vector pClneoDHFR*-RK. pCl-neoDHFR*-RK is opened by digestion with EcoO109I. In order to create blunt ends, treatment with the Klenow enzyme is performed afterwards.

The expression cassette from pClneo2RK is excised by digesting the plasmid with BglII, NgoMIV and StuI. After ligation of the two fragments the "empty" expression vector pCHO2neoN is created. Into pCHO2neoN the antibody light chain gene is inserted via the MluI and SalI restriction site thereby creating a vector construct, to which we refer as pBW108. The antibody gene is therefore amplified using primers which contain the two restriction sites.

The mAB heavy chain is inserted into pBW108 via PmeI and AscI digestion of the vector, thereby obtaining a vector construct deemed pBW111 for description purposes. The heavy chain is PCR amplified with the 5' end generating blunt ends and the 3' end of the gene containing the AscI restriction site.

In pBW111 the 5' non-translated region end of the light chain is exchanged because an additional ATG codon is present in front of the light chain cDNA. This is accomplished by excising a BglII/MluI fragment from pBW111 and replacing it with the corrected fragment. The new plasmid is deemed pBW133. pBW133 is the first vector with all genes on one plasmid. The arrangement of the genes is: LC-DHFR (opposite direction)-neo-HC (see also table 2). This vector is one of the starting materials that can be used for obtaining vectors according to the teachings of the present invention. However, it is clear that there are several other ways to obtain respective vectors.

Construction of pBW139

The second vector construct that can be used for obtaining pBW147 has the configuration of pBW139. pBW139 can be created from pBW115. For the construction of pBW115, the heavy chain gene is cloned into pClneoRK (see above). Therefore, pClneoRK is digested with MluI and NruI (blunt end cutter), whereas the heavy chain PCR fragment is digested with AscI (3') (compatible to MluI) and is blunt 5'. The resulting plasmid is deemed pBW115.

pBW115 is digested with ScaI and BglII. Then a Klenow fill-in is done to create blunt ends. The light chain expression cassette is excised from pBW133 with ScaI and DraIII. In order to create blunt ends, T4-DNA polymerase treatment is done. Resulting from the ligation is a vector having a configuration as pBW139 (see table 2).

Assembly of pBW147

For obtaining pBW147, pBW133 is digested with SpeI, XhoI. The fragment containing parts of the CMV promoter and the first part of the heavy chain is isolated and ligated to pBW139, which is also cut with SpeI, XhoI. In the resulting vector the heavy-chain cassette is found without a disturbing additional ATG codon. In order to bring back the light chain into the vector, pBW139 is digested with SpeI. The LC containing fragment is inserted into pBW148 which is opened with SpeI. The resulting plasmid has a configuration as pBW146 (see table 2).

In pBW146 the DHFR gene from pBW112 (expression vector from another project) is inserted. However, the DHFR gene could also be obtained from a different source, depending on the kind of DHFR variant desired. pBW146 is digested with BglII. Afterwards the DHFR cassette is PCR amplified with primers containing BglII and BamHI restriction sites. The PCR fragment is digested with the two enzymes and inserted in the fitting BglII site of pBW146. The resulting plasmid has a configuration as pBW147, wherein all expression cassettes have the same orientation. The structure is shown in table 3.

This expression vector can be used to obtain stable transfections. In order to further increase the expression yield, a very MTX "sensitive" wild type DHFR variant can be chosen, wherein also the MTX concentrations should be adapted adequately.

Example 6

Construction of Expression Vector pBW154

For this vector, the tandem configuration of the mAB genes and the DHFR gene cassette from pSV2DHFR (wild type version of DHFR with high sensitivity to MTX) are tested. The DHFR expression cassette from pSV2DHFR (ATCC#374146) is amplified by PCR. The fragment contained the promoter and the polyA sites. As before, the oligos had BglII/BamHI restriction sites. The DHFR expression cassette is inserted in the BglII restriction site of pBW146, resulting in a vector construct having the same structure as pBW154. The structure of pBW154 is shown in table 3 and can be derived from FIGS. 1 and 2 which show a general example of a vector construct having a respective overall structure/configuration of the genetic elements. The sequence of pBW154 is provided as Seq. ID No 1. The light chain polynucleotide is marked n (in the priority application indicated with the placeholder V), the heavy chain polynucleotide is marked n (in the priority application indicated with the placeholder Y) in Seq. ID No. 1. The features of pBW154 are summarized in Table 4. Of course, also other vector elements, e.g. different promoters, different enhancers, different Poly A sites and other elements such as different oris can be used. Furthermore, it is possible to switch the expression cassettes for the light and the heavy chain of the immunoglobulin molecule. However, the shown selection and arrangement of the vector elements is preferred. As is outlined above, also functional fragments of immunoglobulin molecules can be used. Therefore, the indicated "nnn" only serve the purpose of illustration and do not indicate any size restriction as smaller or larger immunoglobulin sequences can be present at the corresponding position. In order to alleviate comparison with FIGS. 1 and 2, which show the general construction of vectors according to the preferred embodiment of the invention, we have indicated the numbering of the corresponding elements in FIGS. 1 and 2.

TABLE 4

| Base pair Start | End | Feature | Corresponding numbering in FIG. 1 and 2 |
| --- | --- | --- | --- |
| 1 | 743 | CMV prom/enh | 1 |
| 857 | 1000 | RK-intron | 2 |
| 1054 | 1766 | mAB LC | 3 |
| 1815 | 2036 | SV40polyA | 4 |
| 2367 | 3109 | CMV prom/enh | 5 |
| 3223 | 3366 | RK-intron | 6 |
| 3452 | 4863 | mAB HC | 7 |
| 4931 | 5152 | SV40polyA | 8 |
| 5766 | 6184 | SV40prom | 9 |
| 6229 | 7024 | Neomycin phosphotransferase | 10 |
| 7087 | 7135 | Synthetic poly A | 11 |
| 7546 | 8406 | Beta lactamase antibiotic resistance gene | 12 |
| 9243 | | Unique Linearisation site | 13 |
| 9422 | 9617 | SV40prom | 14 |
| 9640 | 10204 | DHFR | 15 |
| 9776 | 10426 | Intron (Donor-Acceptor) | 16 |
| 10909 | 11098 | SV40polyA | 17 |

All genetic elements are arranged in the same 5' to 3' orientation. With this vector construct using a wildtype DHFR, gene amplification as described above works very efficiently. The titer in a standard batch experiment can be increased by 10-20-fold. Herein, a great increase in the antibody expression titer is observed upon MTX amplification. Starting from G418 treatment, over the treatment without nucleotides up to several different concentrations with MTX (20 and 100 nM MTX), the titer constantly and considerably increases. However, using much higher MTX concentrations (e.g. 500 nM MTX) usually brings no further advantages with CHO cells, even though respective high concentrations can be used. The antibody titers obtained for pools over the selection/amplification process ranged from 2 to more than 60 mg/L when using standard culturing procedures. The expression titers can be further increased upon establishing clonal cell lines from the pools and using customized media to enhance cell expression as the obtainable titer also depends on the used medium.

Example 7

Construction of Expression Vector pBW160

The experiments also demonstrate that the orientation of the DHFR gene in the vector is decisive. In pBW146 (see above) an EcoRI restriction site is present. In order to have EcoRI as a single cutter present in the final expression vector, the site can be removed by digesting pBW146 with EcoRI, Klenow-Fill in and relegation. This results in plasmid having the configuration as pBW158 (not shown). The DHFR cassette can be integrated in pBW158, as is described above. Since both orientations (orientation as is shown in pBW159 and pBW160, see table 2 and 3) are automatically generated, both can be tested for expression levels. Our results show superior performance of the configuration with all open reading frames orientated in one 5' to 3' reading direction.

Vectors having a configuration such as pBW159 vector (see table 2), wherein the DHFR orientation is in reverse order of the mAB genes usually show only very low expression titers, even after MTX amplification (usually less than 1 mg/L). Vectors having a design such as pBW160 (see table 3), wherein the DHFR orientation is in frame with the mAB genes, can provide higher antibody titers of more than 5 mg/L and even more than 10 or even more than 15 mg/L (obtainable from the pools). Again, by establishing a clonal cell line and by using a high performance medium the titer yield can be further increased when using the vector constructs according to the present invention.

These experiments can demonstrate the advantage of the "in frame configuration" of the selection markers and the mAB coding genes as are used according to the teachings of the present invention. This result supports the finding that the 5' to 3' orientation of the vector elements is an important factor for high expression vectors. Furthermore, the expression stability is very favourable with the expression vectors according to the present invention.

The vector configuration according to the present invention enables the straight forward generation of cell pools with high cell specific productivities. Key elements are the 5' to 3' orientation, the chosen DHFR variants and the placement of the DHFR selection marker on the vector as well as the arrangement of the antibody genes and the second selection marker (neo) on the plasmid. The vector can also be used for the production of non-antibody proteins or peptides. As described above, with slight adaptations of the DHFR cassette, this system is also usable for gene amplification in the DHFR positive CHO-K1PD cell line. For gene amplification in DHFR$^+$ host cells a mutated version of the DHFR gene is used (see above). The complete DHFR expression cassette of a vector comprising a mutated version of the DHFR gene such as pBW117 can be PCR amplified with primers incorporating a BamHI site. This fragment is then cloned into the BglII site of pBW158 resulting in the vector pBW165. With vectors having a configuration such as pBW165 comprising a mutated DHFR gene (and follow ups with other antibodies), high yielding cell lines can be generated in the CHO-K1-PD host cell, which is a DHFR+ cell line. An example of a respective vector sequence is provided as Seq. ID No. 16. Of course also different vector elements than the ones shown can be used, e.g. different promoters, different enhancers, different Poly A sites and/or other elements such as e.g. different oris. Furthermore, it is possible to switch the expression cassettes for the light and the heavy chain of the immunoglobulin molecule. However, the shown selection and arrangement of the vector elements is preferred. As is outlined above, full-length immunoglobulin molecules as well as functional fragments of immunoglobulin molecules can be expressed from the vector. In Seq. ID No. 16 only the site is indicated as insertion site, where the respective immunoglobulin sequence can be located/inserted in the final expression vector. Any immunoglobulin sequences can be present at the corresponding position. Furthermore, as is outlined above, it is also possible to express different polypeptides of interests.

Example 8

Small Scale Production of Antibodies with Transfected CHO Cells

For test in suspension cultures, cells are seeded at 1×10$^5$ cells/ml in 50 ml ExCell81134 medium (SAFC Biosciences) in a 250 ml round bottomed filter cap culture flask. Cells are shaken at 65 rpm in a Kühner Shaker ISF-4-W/incubator at 37° C. in a 10% CO2 environment for the duration of the study. Single feeds with proprietary solutions are given according to a fixed feeding scheme beginning on the 4th day of cell expansion. On the 13th day, 1 ml samples are harvested and titer is measured using standard HPLC and a protein A column.

Cell culture supernatant resulting from shake flask cultures of the best clones is purified by protein A affinity chromatography.

Example 9

Protein A Purification of the Expressed Antibody

For Protein A purification about 27 mL cell free culture supernatant containing approximately 32.4 mg antibody is loaded onto a 0.5×10 cm MabSelect affinity column. After loading, the column is sufficiently rinsed and washed. Then the antibody is eluted at pH 3-4. The eluate is analysed with standard HPLC using a protein A column. About 30.5 mg antibody are obtained.

III. Examples for Cell Specific Productivities and Yields

Clones which are selected after clonal expansion are tested for their productivity.

Example 10

Expression of an IgG1 Antibody

An IgG1 antibody is expressed. Clones are grown in the commercially available medium ExCell81134 (SAFC Biosciences). Feed solutions and conventional additives such as peptone are added. High productivity rates can be obtained when using the vector according to the present invention:

| Clone | Qp (pg/cell/day) |
|---|---|
| 1 | 114 |
| 2 | 91 |
| 3 | 103 |

Qp=cell specific productivity.

Example 11

Expression of an IgG1 Antibody and an IgG4 Antibody

An IgG1 antibody and an IgG4 antibody are expressed. Clones are grown in a proper culture medium. Feed solutions and conventional additives such as peptone are added. High productivity rates can be obtained when using the vector according to the present invention:

| Clone | IgG1 antibody Qp (pg/cell/day) | IgG4 antibody Qp (pg/cell/day) |
|---|---|---|
| 1 | 76 | |
| 2 | 96 | |
| 3 | | 73 |

Qp=cell specific productivity.

Example 12

Large Scale Production of Polypeptides with Transfected CHO Cells

The production of polypeptides in large scale can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product titers in the reactor ranging from a few hundred milligrams per liter up to several grams per litre are achieved in the large scale. Purification can be done by standard chromatography methodology, which can include affinity, ione exchange, hydrophobic interaction or size exclusion chromatography steps. The size of the bioreactor can be up to several thousand litres volume in the final scale (see also e.g. F. Wurm, Nature Biotechnology Vol. 22, 11, 2004, 1393-1398).

Example 13

Cloning Strategy for Introducing New Antibody Genes in the Vectors

One strategy—among others—for inserting new polypeptides of interest is as follows (explained by way of example using a vector having a configuration such as pBW154):
Cloning of the Light Chain Gene The light chain gene can be PCR amplified with primers introducing a MluI site 5' of the ATG codon and a SalI site 3' of the gene. The PCR product is introduced into pBW154 via these two restriction enzymes. This leads to an intermediate vector consisting of just the light chain.

Cloning of the Heavy Chain Gene

The heavy chain gene can be PCR amplified with primers introducing a blunt end for usage of the vector's NruI site 5' of the ATG codon and a XbaI 3' site of the gene. The PCR product is introduced into pBW154 via these two restriction enzymes. This leads to an intermediate vector with the old light chain and the new heavy chain.

Assembly of the Final Vector

The new mAB-HC containing fragment is excised from the HC vector via SalI digestion. It is then inserted into the LC-intermediate vector via SalI to result in the final new LC-HC vector.

The invention claimed is:

1. A vector nucleic acid suitable for expressing at least one polypeptide of interest in a mammalian cell, comprising
  (a) at least one expression cassette (POI) suitable for expressing a polypeptide of interest;
  (b) an expression cassette (MSM) comprising a mammalian selectable marker gene wherein said mammalian selectable marker gene is an antibiotic resistance gene; and
  (c) an expression cassette (MASM) comprising a mammalian amplifiable, selectable marker gene;
  wherein each said expression cassette (POI), (MSM), and (MASM) comprises at least one promoter or promoter/enhancer element, the expression cassette (POI) is flanked 5' by the expression cassette (MASM), the expression cassette (MSM) is located 3' from the expression cassette (POI) and the expression cassettes (MASM), (POI), and (MSM) are arranged in the same 5' to 3' orientation
  and wherein
  the vector is circular and the expression cassette (MASM) is arranged 3' of the expression cassette (MSM) and wherein said circular vector comprises a unique linearization restriction site for linearizing the vector which is located between the expression cassettes (MSM) and (MASM);

or
  wherein the vector is linearized via a unique linearization restriction site located between the expression cassettes (MSM) and (MASM); and
  wherein the vector is selected from the group consisting of
  (a) a circular or linear vector nucleic acid comprising the following genetic elements in the indicated arrangement, wherein the 5' to 3' direction is indicated by the →:
    I) Promoter of the (MASM) expression cassette (→)
    II) Gene encoding the mammalian amplifiable selectable marker of the (MASM) expression cassette (→)
    III) Intron of the (MASM) expression cassette (→)
    IV) PolyA site of the (MASM) expression cassette (→)
    V) Promoter of the (POI) expression cassette (→)
    VI) Intron of the (POI) expression cassette (→)
    VII) Polynucleotide encoding a polypeptide of interest, which is inserted in the (POI) expression cassette (→)
    VIII) PolyA site of the (POI) expression cassette (→)
    IX) Promoter of the (POI') expression cassette (→)
    X) Intron of the (POI') expression cassette (→)
    XI) Polynucleotide encoding an additional polypeptide of interest, which is inserted in the (POI') expression cassette (→)

XII) PolyA site of the (POI') expression cassette (→)
XIII) Promoter of the (MSM) expression cassette (→)
XIV) Gene encoding the mammalian selectable marker of the (MSM) expression cassette (→)
XV) PolyA site of the (MSM) expression cassette (→)
XVI) PSM expression cassette (→)or (←)
XVII) Linearization restriction site if the vector nucleic acid is circular; and (b) a vector nucleic acid as shown as Seq. ID No. 1 or Seq. ID No. 16.

* * * * *